(12) United States Patent
McClintock et al.

(10) Patent No.: US 11,331,200 B2
(45) Date of Patent: May 17, 2022

(54) EXPANDABLE SPINAL IMPLANTS

(71) Applicant: K2M, Inc., Leesburg, VA (US)

(72) Inventors: Larry E. McClintock, Gore, VA (US); Steven Ludwig, Baltimore, MD (US); Scott Dhupar, Windsor, CO (US); Sabatino Bianco, Arlington, TX (US)

(73) Assignee: K2M, Inc., Leesburg, VA (US)

( * ) Notice: Subject to any disclaimer, the term of this patent is extended or adjusted under 35 U.S.C. 154(b) by 240 days.

(21) Appl. No.: 16/516,702

(22) Filed: Jul. 19, 2019

(65) Prior Publication Data
US 2020/0008951 A1 Jan. 9, 2020

Related U.S. Application Data

(63) Continuation of application No. 14/965,246, filed on Dec. 10, 2015, now Pat. No. 10,363,142.

(60) Provisional application No. 62/206,779, filed on Aug. 18, 2015, provisional application No. 62/158,470, (Continued)

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2/442* (2013.01); *A61F 2/446* (2013.01); *A61F 2/4425* (2013.01); *A61F 2002/30538* (2013.01); *A61F 2002/30556* (2013.01); *A61F 2002/30579* (2013.01); *A61F 2002/30594* (2013.01);
(Continued)

(58) Field of Classification Search
CPC ............... A61F 2/4455–447; A61F 2002/4475
See application file for complete search history.

(56) References Cited

U.S. PATENT DOCUMENTS

| | | | |
|---|---|---|---|
| 4,401,112 A | 8/1983 | Rezaian |
| 4,657,550 A | 4/1987 | Daher |
| 5,171,278 A | 12/1992 | Pisharodi |

(Continued)

FOREIGN PATENT DOCUMENTS

| | | |
|---|---|---|
| SU | 01560184 A1 | 4/1990 |
| WO | 9848739 A1 | 11/1998 |

(Continued)

OTHER PUBLICATIONS

European Search Report for EP 15 19 9537 dated Apr. 22, 2016.
Australian Search Report for Application No. 2015268677, dated Aug. 1, 2019, 1 pg.

*Primary Examiner* — Amy R Sipp
(74) *Attorney, Agent, or Firm* — Lerner, David, Littenberg, Krumholz & Mentlik, LLP

(57) ABSTRACT

A spinal implant has a proximal region and a distal region, and includes an upper body and a lower body each having inner surfaces disposed in opposed relation relative to each other. A proximal adjustment assembly is disposed between the upper and lower bodies at the proximal region of the spinal implant and is adjustably coupled to the upper and lower bodies, and a distal adjustment assembly is disposed between the upper and lower bodies at the distal region of the spinal implant and is adjustably coupled to the upper and lower bodies. The proximal and distal adjustment assemblies are independently movable with respect to each other to change a vertical height of at least one of the proximal region or the distal region of the spinal implant.

19 Claims, 22 Drawing Sheets

Related U.S. Application Data filed on May 7, 2015, provisional application No. 62/090,429, filed on Dec. 11, 2014.

(52) U.S. Cl.
CPC .............. *A61F 2002/30843* (2013.01); *A61F 2002/30904* (2013.01); *A61F 2002/443* (2013.01); *A61F 2250/0008* (2013.01)

(56) References Cited

U.S. PATENT DOCUMENTS

| | | |
|---|---|---|
| 5,236,460 A | 8/1993 | Barber |
| 5,290,312 A | 3/1994 | Kojimoto et al. |
| 5,397,364 A | 3/1995 | Kozak et al. |
| 5,554,191 A | 9/1996 | Lahille et al. |
| 5,571,192 A | 11/1996 | Schonhoffer |
| 5,653,762 A | 8/1997 | Pisharodi |
| 5,653,763 A | 8/1997 | Errico et al. |
| 5,665,122 A | 9/1997 | Kambin |
| 5,702,455 A | 12/1997 | Saggar |
| 5,865,848 A | 2/1999 | Baker |
| 5,916,267 A | 6/1999 | Tienboon |
| 5,989,290 A | 11/1999 | Biedermann et al. |
| 6,015,436 A | 1/2000 | Schonoffer |
| 6,045,579 A | 4/2000 | Hochshuler et al. |
| 6,102,950 A | 8/2000 | Vaccaro |
| 6,159,244 A | 12/2000 | Suddaby |
| 6,174,334 B1 | 1/2001 | Suddaby |
| 6,176,881 B1 | 1/2001 | Schar et al. |
| 6,176,882 B1 | 1/2001 | Biedermann et al. |
| 6,190,413 B1 | 2/2001 | Sutcliffe |
| 6,190,414 B1 | 2/2001 | Young et al. |
| 6,193,755 B1 | 2/2001 | Metz-Stavenhagen et al. |
| 6,193,756 B1 | 2/2001 | Studer et al. |
| 6,200,348 B1 | 3/2001 | Biedermann et al. |
| 6,214,050 B1 | 4/2001 | Huene |
| 6,296,665 B1 | 10/2001 | Strnad et al. |
| 6,332,895 B1 | 12/2001 | Suddaby |
| 6,344,057 B1 | 2/2002 | Rabbe et al. |
| 6,352,556 B1 | 3/2002 | Kretschmer et al. |
| 6,371,989 B1 | 4/2002 | Chauvin et al. |
| 6,375,682 B1 | 4/2002 | Fleischmann et al. |
| 6,375,683 B1 | 4/2002 | Crozet et al. |
| 6,395,031 B1 | 5/2002 | Foley et al. |
| 6,395,034 B1 | 5/2002 | Suddaby |
| 6,409,766 B1 | 6/2002 | Brett |
| 6,419,705 B1 | 7/2002 | Erickson |
| 6,436,140 B1 | 8/2002 | Liu et al. |
| 6,436,142 B1 | 8/2002 | Paes et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,491,724 B1 | 12/2002 | Ferree |
| 6,524,341 B2 | 2/2003 | Lang et al. |
| 6,562,074 B2 | 5/2003 | Gerbec et al. |
| 6,576,016 B1 | 6/2003 | Hochshuler et al. |
| 6,610,090 B1 | 8/2003 | Bohm et al. |
| 6,616,695 B1 | 9/2003 | Crozet et al. |
| 6,641,614 B1 | 11/2003 | Wagner et al. |
| 6,685,742 B1 | 2/2004 | Jackson |
| 6,716,247 B2 | 4/2004 | Michelson |
| 6,773,460 B2 | 8/2004 | Jackson |
| 6,783,547 B2 | 8/2004 | Castro |
| 6,808,537 B2 | 10/2004 | Michelson |
| 6,814,756 B1 | 11/2004 | Michelson |
| 6,821,298 B1 | 11/2004 | Jackson |
| 6,866,682 B1 | 3/2005 | An et al. |
| 6,902,579 B2 | 6/2005 | Harms et al. |
| 6,955,691 B2 | 10/2005 | Chae et al. |
| 6,962,606 B2 | 11/2005 | Michelson |
| 6,972,035 B2 | 12/2005 | Michelson |
| 7,008,453 B1 | 3/2006 | Michelson |
| 7,018,415 B1 | 3/2006 | McKay |
| 7,022,138 B2 | 4/2006 | Mashburn |
| 7,029,498 B2 | 4/2006 | Boehm et al. |
| 7,044,971 B2 | 5/2006 | Suddaby |
| 7,056,343 B2 | 6/2006 | Schafer et al. |
| 7,087,055 B2 | 8/2006 | Lim et al. |
| 7,094,257 B2 | 8/2006 | Mujwid et al. |
| 7,118,579 B2 | 10/2006 | Michelson |
| 7,156,874 B2 | 1/2007 | Paponneau et al. |
| 7,211,112 B2 | 5/2007 | Baynham et al. |
| 7,217,291 B2 | 5/2007 | Zucherman et al. |
| 7,217,293 B2 | 5/2007 | Branch, Jr. |
| 7,311,733 B2 | 12/2007 | Metz-Stavenhagen |
| 7,431,735 B2 | 10/2008 | Liu et al. |
| 7,458,988 B2 | 12/2008 | Trieu et al. |
| 7,544,208 B1 | 6/2009 | Mueller et al. |
| 7,547,325 B2 | 6/2009 | Biedermann et al. |
| 7,575,601 B2 | 8/2009 | Dickson |
| 7,588,573 B2 | 9/2009 | Berry |
| 7,615,078 B2 | 11/2009 | White et al. |
| 7,618,458 B2 | 11/2009 | Biedermann et al. |
| 7,621,953 B2 | 11/2009 | Braddock, Jr. et al. |
| 7,641,693 B2 | 1/2010 | Gutlin et al. |
| 7,655,027 B2 | 2/2010 | Michelson |
| 7,674,296 B2 | 3/2010 | Rhoda et al. |
| 7,678,148 B2 | 3/2010 | Peterman |
| 7,691,147 B2 | 4/2010 | Gutlin et al. |
| 7,708,779 B2 | 5/2010 | Edie et al. |
| 7,731,752 B2 | 6/2010 | Edie et al. |
| 7,744,650 B2 | 6/2010 | Lindner et al. |
| 7,758,648 B2 | 7/2010 | Castleman et al. |
| 7,763,028 B2 | 7/2010 | Lim et al. |
| 7,794,501 B2 | 9/2010 | Edie et al. |
| 7,799,081 B2 | 9/2010 | McKinley |
| 7,803,191 B2 | 9/2010 | Biedermann et al. |
| 7,815,683 B2 | 10/2010 | Melkent et al. |
| 7,819,920 B2 | 10/2010 | Assaker |
| 7,819,921 B2 | 10/2010 | Grotz |
| 7,819,922 B2 | 10/2010 | Sweeney |
| 7,828,849 B2 | 11/2010 | Lim |
| 7,850,733 B2 | 12/2010 | Baynham et al. |
| 7,862,618 B2 | 1/2011 | White et al. |
| 7,875,078 B2 | 1/2011 | Wysocki et al. |
| 7,879,098 B1 | 2/2011 | Simmons, Jr. |
| 7,883,542 B2 | 2/2011 | Zipnick |
| 7,887,596 B2 | 2/2011 | Douget et al. |
| 7,909,870 B2 | 3/2011 | Kraus |
| 7,914,581 B2 | 3/2011 | Dickson et al. |
| 7,959,677 B2 | 6/2011 | Landry et al. |
| 7,967,867 B2 | 6/2011 | Barreiro et al. |
| 7,981,157 B2 | 7/2011 | Castleman et al. |
| 8,034,111 B2 | 10/2011 | Hsu et al. |
| 8,062,366 B2 | 11/2011 | Melkent |
| 8,062,368 B2 | 11/2011 | Heinz et al. |
| 8,062,375 B2 | 11/2011 | Glerum et al. |
| 8,070,817 B2 | 12/2011 | Gradl et al. |
| 8,105,382 B2 | 1/2012 | Olmos et al. |
| 8,110,004 B2 | 2/2012 | Valdevit et al. |
| 8,118,871 B2 | 2/2012 | Gordon et al. |
| 8,123,809 B2 | 2/2012 | Melkent et al. |
| 8,128,701 B2 | 3/2012 | Kast |
| 8,133,232 B2 | 3/2012 | Levy et al. |
| 8,152,852 B2 | 4/2012 | Biyani |
| 8,157,864 B2 | 4/2012 | Rogeau et al. |
| 8,163,020 B2 | 4/2012 | Le Huec |
| 8,177,846 B2 | 5/2012 | Blackwell et al. |
| 8,182,535 B2 | 5/2012 | Kraus |
| 8,182,537 B2 | 5/2012 | Refai et al. |
| 8,187,328 B2 | 5/2012 | Melkent |
| 8,187,331 B2 | 5/2012 | Strohkirch, Jr. et al. |
| 8,197,546 B2 | 6/2012 | Doubler et al. |
| 8,202,321 B2 | 6/2012 | Gemer |
| 8,211,178 B2 | 7/2012 | Melkent et al. |
| 8,221,502 B2 | 7/2012 | Branch, Jr. |
| 8,241,294 B2 | 8/2012 | Sommerich et al. |
| 8,241,358 B2 | 8/2012 | Butler et al. |
| 8,241,363 B2 | 8/2012 | Sommerich et al. |
| 8,252,054 B2 | 8/2012 | Greenhalgh et al. |
| 8,267,939 B2 | 9/2012 | Cipoletti et al. |
| 8,268,002 B2 | 9/2012 | Blackwell et al. |
| 8,268,004 B2 | 9/2012 | Castleman et al. |

(56) References Cited

U.S. PATENT DOCUMENTS

| | | |
|---|---|---|
| 8,273,124 B2 | 9/2012 | Renganath et al. |
| 8,273,126 B2 | 9/2012 | Lindner |
| 8,292,963 B2 | 10/2012 | Miller et al. |
| 8,308,802 B2 | 11/2012 | Rhoda et al. |
| 8,317,866 B2 | 11/2012 | Palmatier et al. |
| 8,328,871 B2 | 12/2012 | Capote et al. |
| 8,337,558 B2 | 12/2012 | Lindner |
| 8,353,963 B2 | 1/2013 | Glerum |
| 8,366,777 B2 | 2/2013 | Matthis et al. |
| 8,377,140 B2 | 2/2013 | DeFalco et al. |
| 8,382,842 B2 | 2/2013 | Greenhalgh et al. |
| 8,398,713 B2 | 3/2013 | Weiman |
| 8,409,283 B2 | 4/2013 | Drochner et al. |
| 8,409,291 B2 | 4/2013 | Blackwell et al. |
| 8,425,608 B2 | 4/2013 | Dewey et al. |
| 8,425,611 B2 | 4/2013 | Dewey et al. |
| 8,435,298 B2 | 5/2013 | Weiman |
| 8,486,147 B2 | 7/2013 | de Villiers et al. |
| 8,496,706 B2 | 7/2013 | Ragab et al. |
| 8,506,635 B2 | 8/2013 | Palmatier et al. |
| 8,518,114 B2 | 8/2013 | Marik |
| 8,518,120 B2 | 8/2013 | Glerum et al. |
| 8,535,380 B2 | 9/2013 | Greenhalgh et al. |
| 8,540,770 B2 | 9/2013 | Woodburn, Sr. et al. |
| 8,551,173 B2 | 10/2013 | Lechmann et al. |
| 8,574,300 B2 | 11/2013 | McManus et al. |
| 8,585,763 B2 | 11/2013 | Olevsky et al. |
| 8,591,585 B2 | 11/2013 | McLaughlin et al. |
| 8,628,576 B2 | 1/2014 | Triplett et al. |
| 8,628,578 B2 | 1/2014 | Miller et al. |
| 8,657,882 B2 | 2/2014 | Bonin, Jr. |
| 8,663,329 B2 | 3/2014 | Ernst |
| 8,679,183 B2 | 3/2014 | Glerum et al. |
| 8,685,095 B2 | 4/2014 | Miller et al. |
| 8,740,980 B2 | 6/2014 | Merves |
| 8,795,366 B2 | 8/2014 | Varela |
| 8,845,733 B2 | 9/2014 | O'Neil et al. |
| 8,876,905 B2 | 11/2014 | Frasier |
| 8,894,712 B2 | 11/2014 | Varela |
| 8,940,049 B1 | 1/2015 | Jimenez et al. |
| 8,992,620 B2 | 3/2015 | Ashley et al. |
| 9,028,550 B2 | 5/2015 | Shulock et al. |
| 9,492,288 B2 | 11/2016 | Wagner et al. |
| 9,622,878 B2 | 4/2017 | Grotz |
| 2001/0039456 A1 | 11/2001 | Boyer et al. |
| 2002/0068976 A1 | 6/2002 | Jackson |
| 2004/0087947 A1 | 5/2004 | Lim et al. |
| 2004/0186569 A1 | 9/2004 | Berry |
| 2004/0193158 A1 | 9/2004 | Lim |
| 2004/0210312 A1 | 10/2004 | Neumann |
| 2004/0215191 A1 | 10/2004 | Kitchen |
| 2004/0254643 A1 | 12/2004 | Jackson |
| 2005/0015149 A1 | 1/2005 | Michelson |
| 2005/0060036 A1 | 3/2005 | Schultz et al. |
| 2005/0125061 A1 | 6/2005 | Zucherman et al. |
| 2005/0182416 A1 | 8/2005 | Lim et al. |
| 2005/0283245 A1 | 12/2005 | Gordon et al. |
| 2006/0058879 A1 | 3/2006 | Metz-Stavenhagen |
| 2006/0122701 A1 | 6/2006 | Kiester |
| 2006/0167547 A1 | 7/2006 | Suddaby |
| 2007/0123987 A1 | 5/2007 | Bernstein |
| 2007/0270964 A1 | 11/2007 | Strohkirch et al. |
| 2008/0021559 A1 | 1/2008 | Thramann |
| 2008/0058931 A1 | 3/2008 | White et al. |
| 2008/0114467 A1 | 5/2008 | Capote et al. |
| 2008/0161933 A1 | 7/2008 | Grotz et al. |
| 2008/0167720 A1 | 7/2008 | Melkent |
| 2008/0177387 A1 | 7/2008 | Parimore et al. |
| 2008/0243254 A1 | 10/2008 | Butler |
| 2008/0281424 A1 | 11/2008 | Parry et al. |
| 2008/0288071 A1 | 11/2008 | Biyani et al. |
| 2009/0112325 A1 | 4/2009 | Refai et al. |
| 2009/0216331 A1 | 8/2009 | Grotz et al. |
| 2009/0281625 A1 | 11/2009 | Enayati |
| 2009/0292361 A1 | 11/2009 | Lopez |
| 2010/0016969 A1 | 1/2010 | Richter et al. |
| 2010/0082106 A1 | 4/2010 | Muhanna |
| 2010/0082109 A1 | 4/2010 | Greenhalgh |
| 2010/0094424 A1 | 4/2010 | Woodburn et al. |
| 2010/0145455 A1 | 6/2010 | Simpson et al. |
| 2010/0191336 A1 | 7/2010 | Greenhalgh |
| 2010/0211176 A1 | 8/2010 | Greenhalgh |
| 2010/0249846 A1 | 9/2010 | Simonson |
| 2011/0015741 A1 | 1/2011 | Melkent et al. |
| 2011/0035009 A1 | 2/2011 | Sweeney |
| 2011/0138948 A1* | 6/2011 | Jimenez .............. F16H 25/2056 74/424.82 |
| 2011/0172774 A1 | 7/2011 | Varela |
| 2011/0184524 A1 | 7/2011 | Wiedenbeck et al. |
| 2011/0190890 A1 | 8/2011 | Blackwell et al. |
| 2011/0251692 A1 | 10/2011 | McLaughlin et al. |
| 2011/0264220 A1 | 10/2011 | Miller |
| 2011/0282453 A1 | 11/2011 | Greenhalgh et al. |
| 2011/0319997 A1 | 12/2011 | Glerum et al. |
| 2012/0016476 A1 | 1/2012 | Wilfong et al. |
| 2012/0016478 A1 | 1/2012 | Wilfong et al. |
| 2012/0019307 A1 | 1/2012 | Ludwig |
| 2012/0029635 A1 | 2/2012 | Schoenhoeffer et al. |
| 2012/0029638 A1 | 2/2012 | Miller et al. |
| 2012/0029640 A1 | 2/2012 | Capote et al. |
| 2012/0071977 A1 | 3/2012 | Oglaza et al. |
| 2012/0109302 A1 | 5/2012 | Miller et al. |
| 2012/0197398 A1 | 8/2012 | Miller et al. |
| 2012/0209384 A1 | 8/2012 | Arnold et al. |
| 2012/0226356 A1 | 9/2012 | Hirschl |
| 2012/0232660 A1 | 9/2012 | Davenport |
| 2012/0310350 A1 | 12/2012 | Farris et al. |
| 2012/0323329 A1 | 12/2012 | Jimenez et al. |
| 2012/0330421 A1 | 12/2012 | Weiman |
| 2013/0103156 A1 | 4/2013 | Packer et al. |
| 2013/0116791 A1 | 5/2013 | Theofilos |
| 2013/0158663 A1 | 6/2013 | Miller |
| 2013/0158664 A1 | 6/2013 | Palmatier et al. |
| 2013/0197642 A1 | 8/2013 | Ernst |
| 2013/0197648 A1 | 8/2013 | Boehm et al. |
| 2013/0211526 A1 | 8/2013 | Alheidt et al. |
| 2014/0067069 A1 | 3/2014 | Lopez |
| 2014/0088714 A1 | 3/2014 | Miller et al. |
| 2014/0142706 A1 | 5/2014 | Hansell et al. |
| 2014/0180419 A1 | 6/2014 | Dmuschewsky |
| 2014/0277501 A1 | 9/2014 | Northcutt et al. |
| 2015/0057753 A1 | 2/2015 | Barrus et al. |
| 2015/0057755 A1 | 2/2015 | Suddaby et al. |
| 2016/0058575 A1 | 3/2016 | Sutterlin, III et al. |
| 2016/0120660 A1 | 5/2016 | Melkent et al. |
| 2016/0250034 A1* | 9/2016 | Loebl .................... A61F 2/4611 623/17.16 |
| 2017/0135824 A1 | 5/2017 | Suddaby et al. |
| 2017/0156885 A1* | 6/2017 | Zur ........................ A61F 2/447 |

FOREIGN PATENT DOCUMENTS

| | | |
|---|---|---|
| WO | 2013158294 A1 | 10/2013 |
| WO | 2013181024 A1 | 12/2013 |
| WO | 2016069796 A1 | 5/2016 |
| WO | 2016127139 A1 | 8/2016 |

* cited by examiner

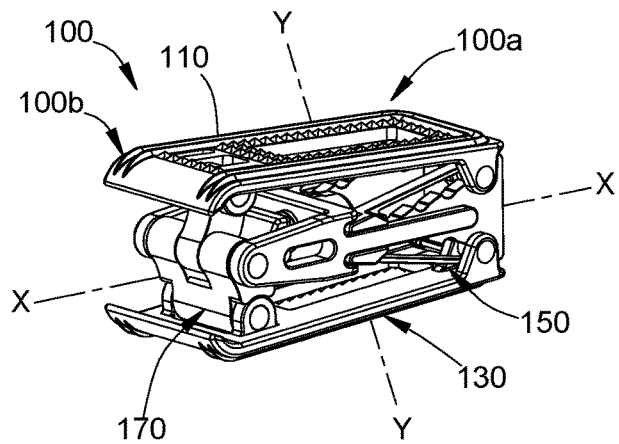
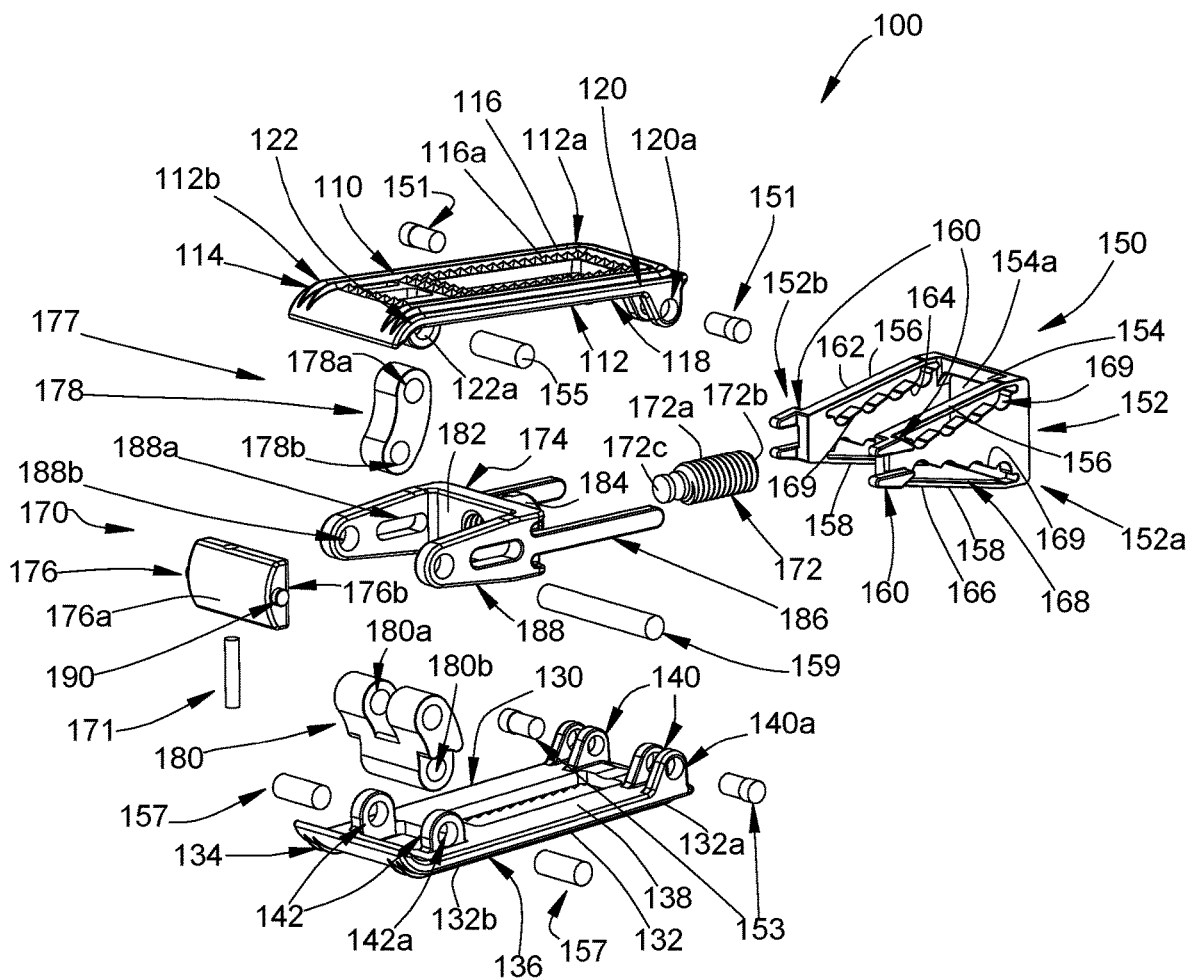

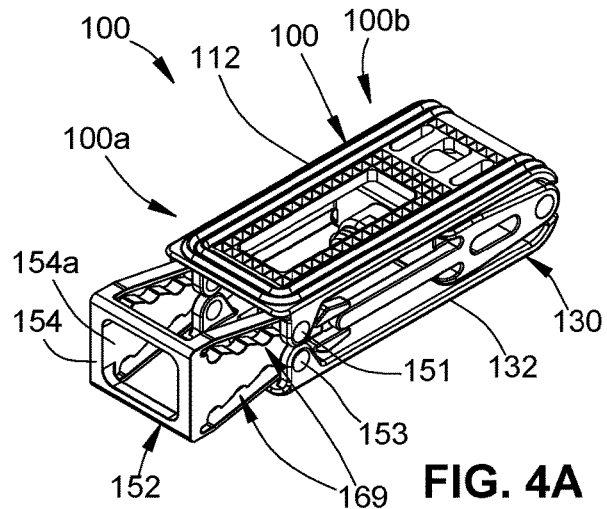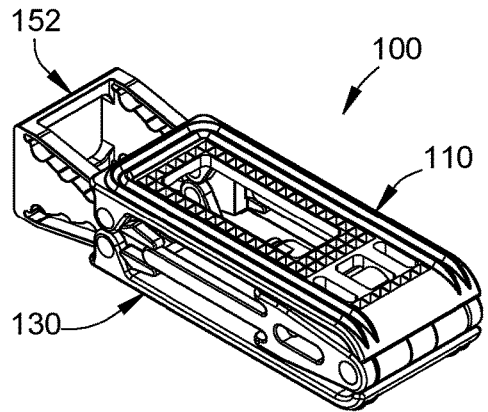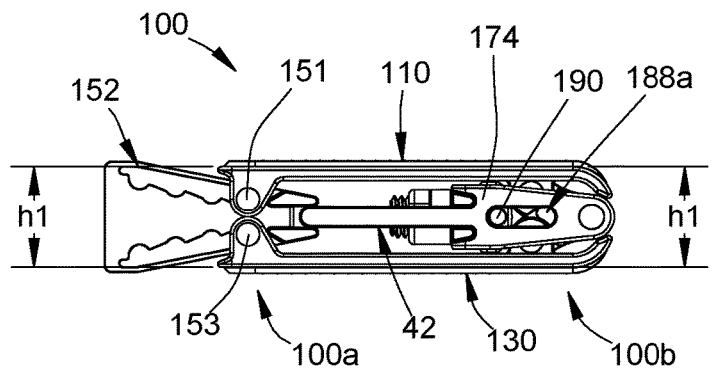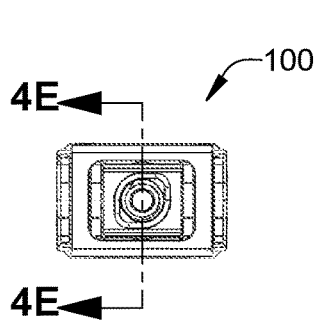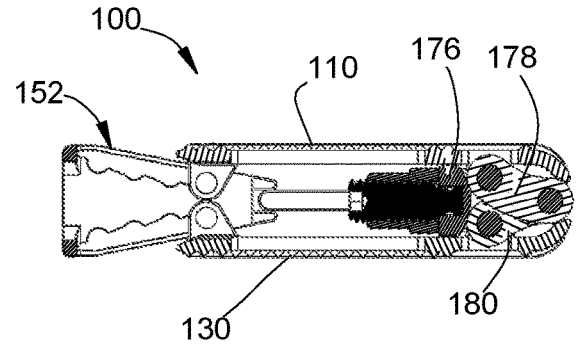

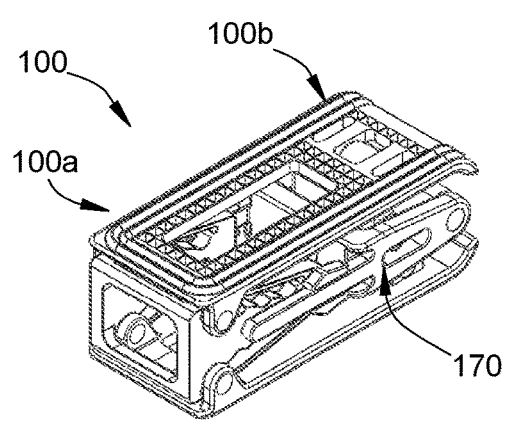 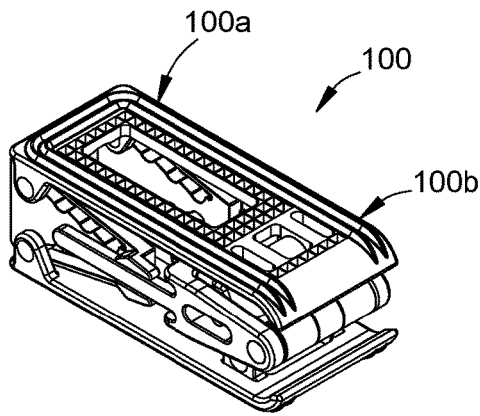
FIG. 9A    FIG. 9B
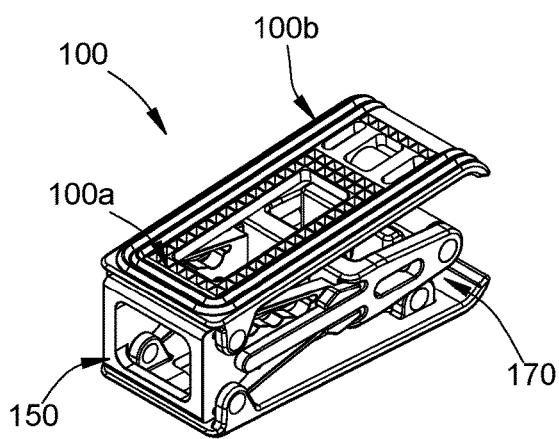 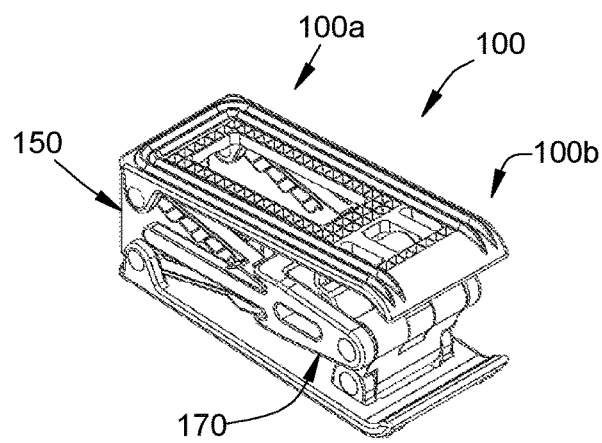
FIG. 10A    FIG. 10B

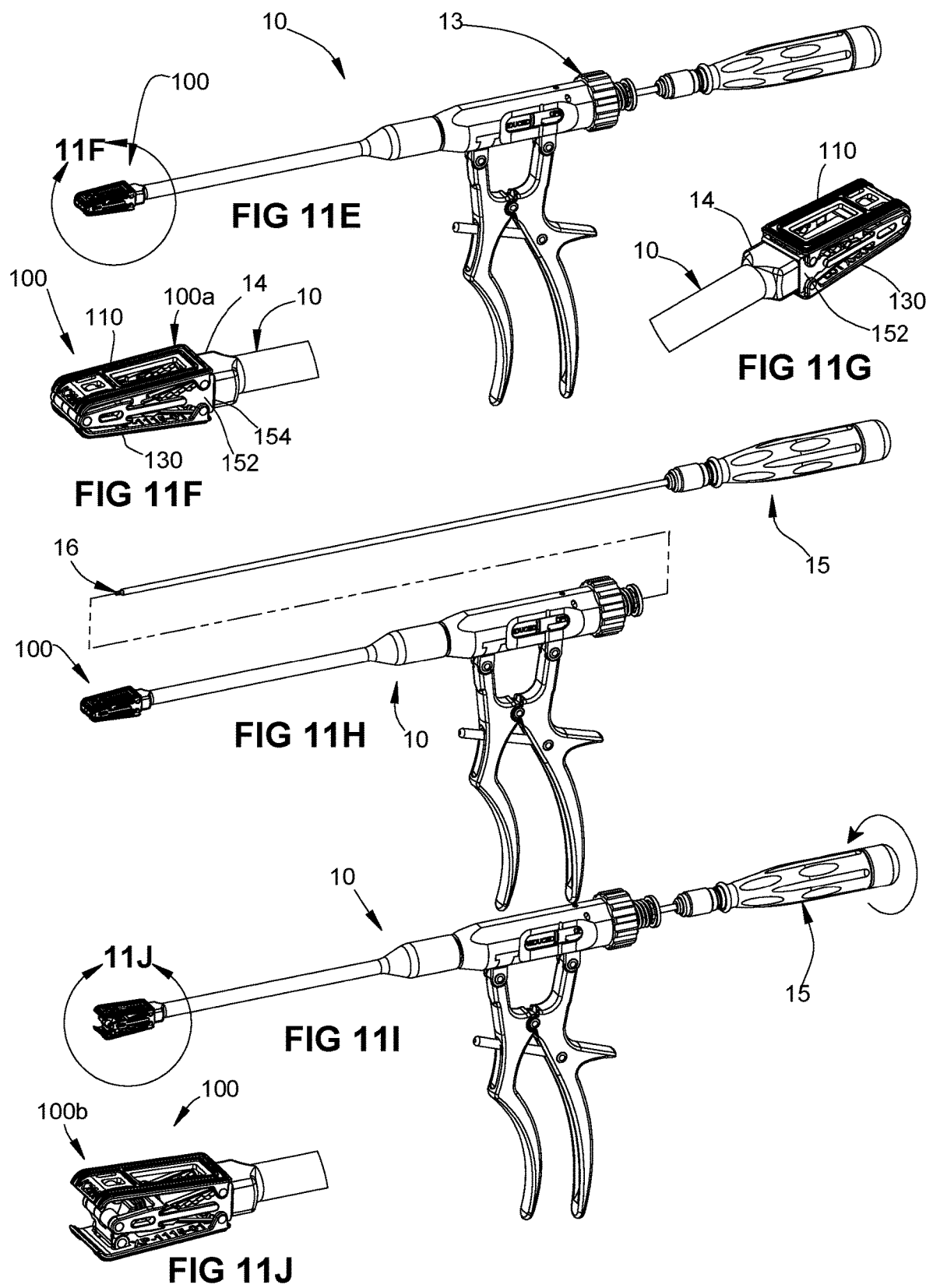

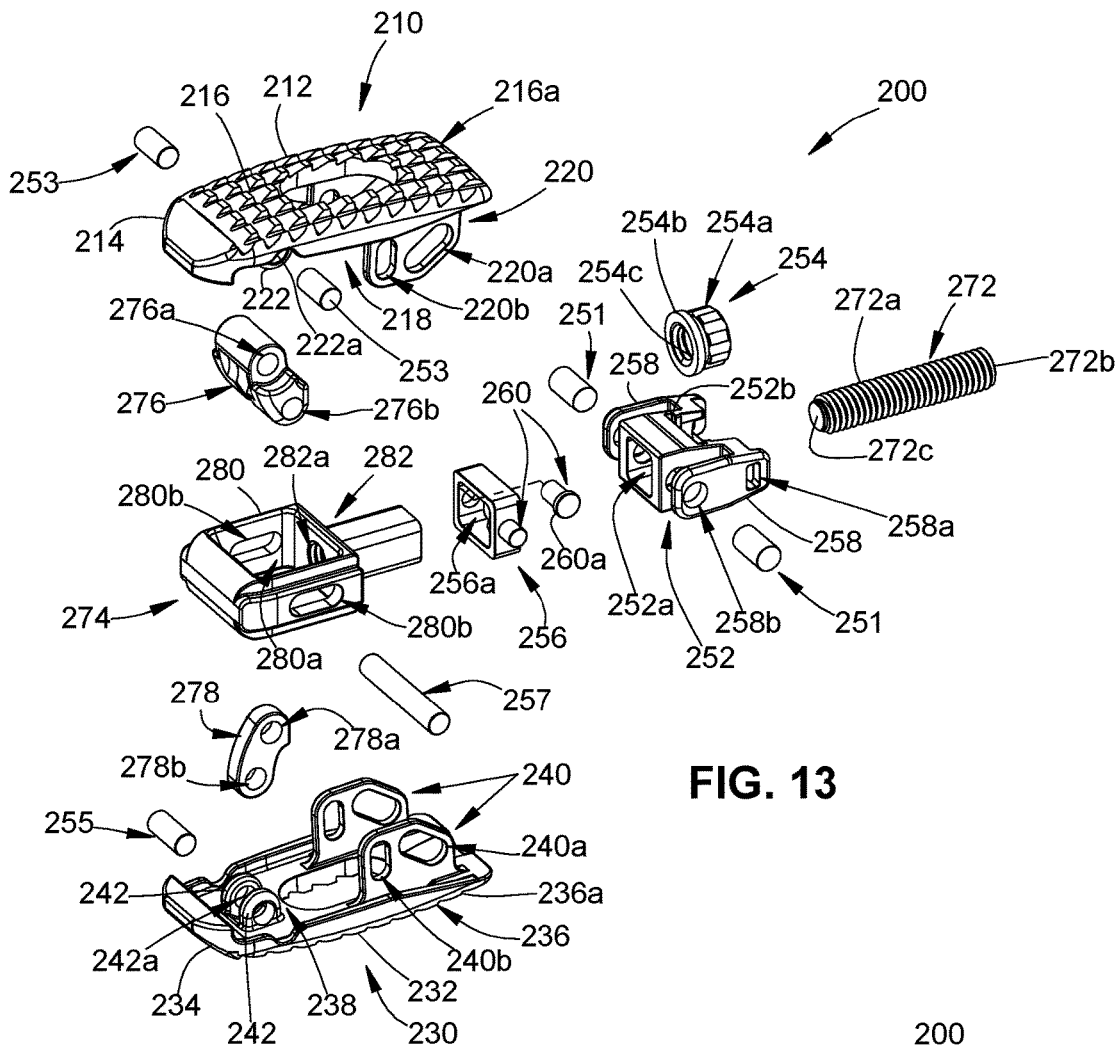
FIG. 13
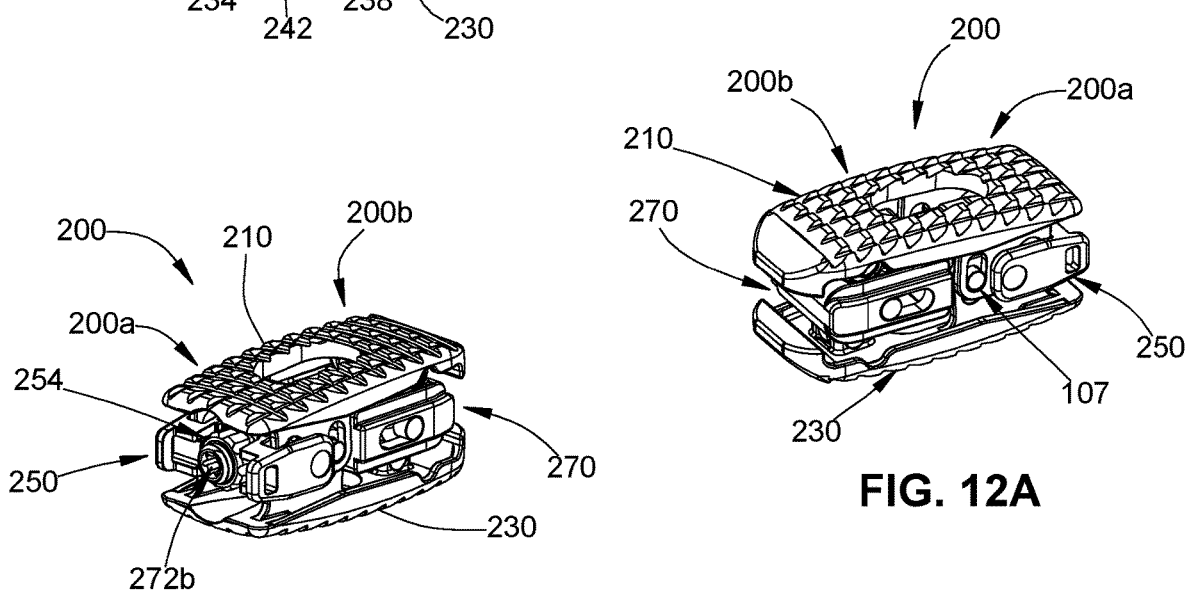
FIG. 12A
FIG. 12B

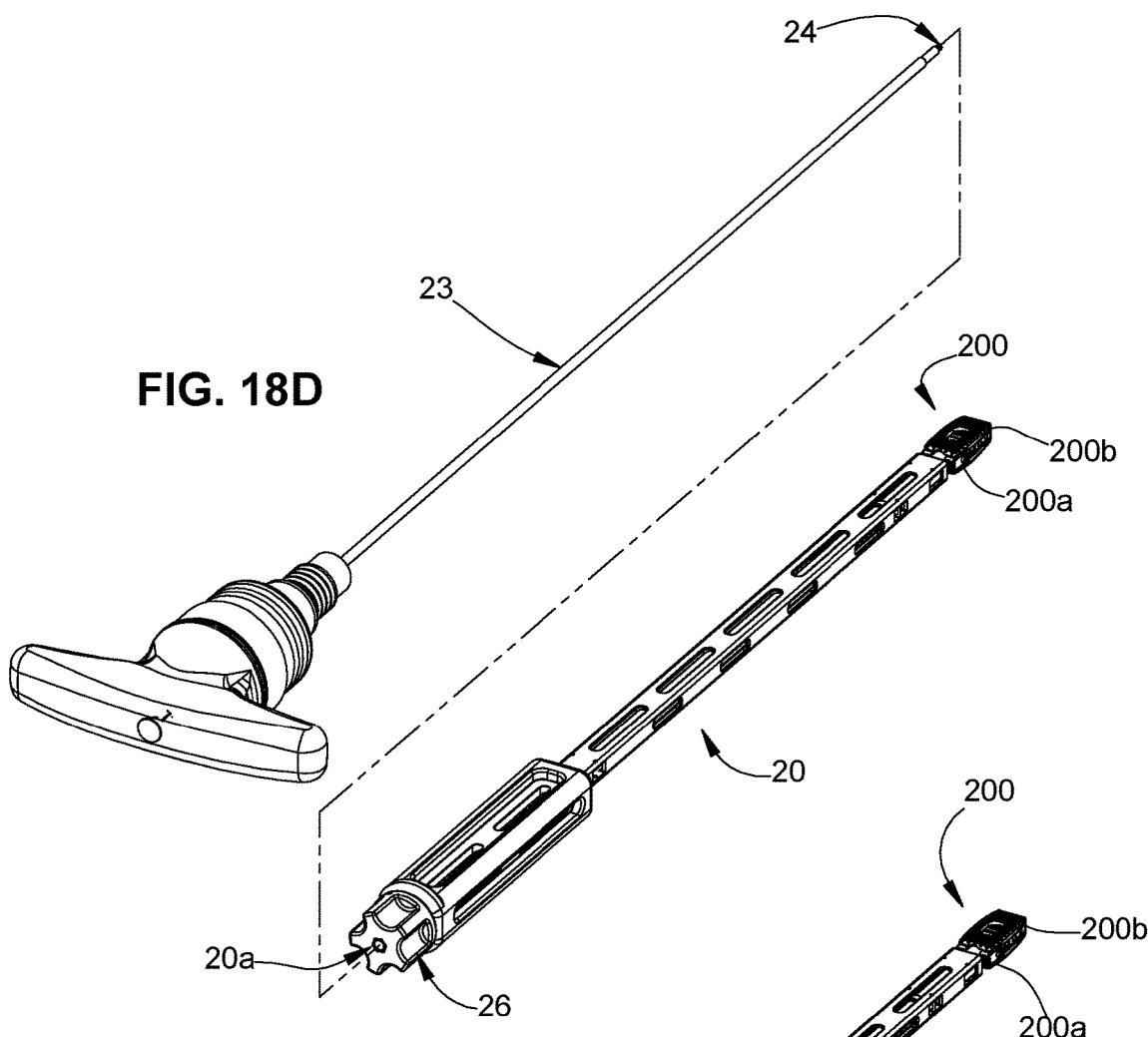
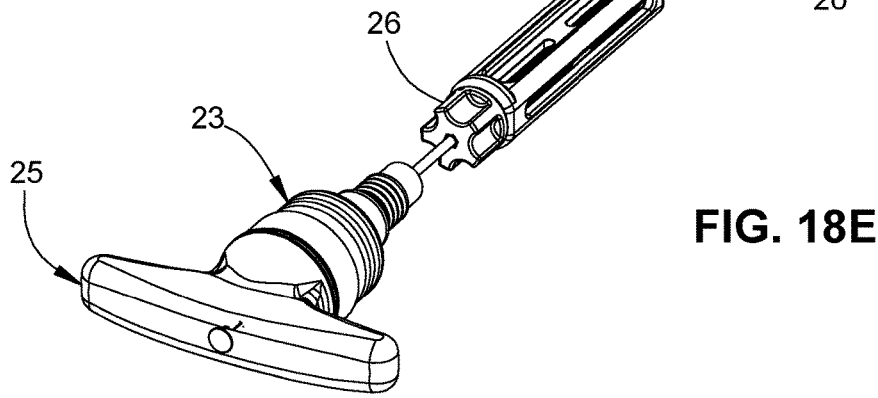

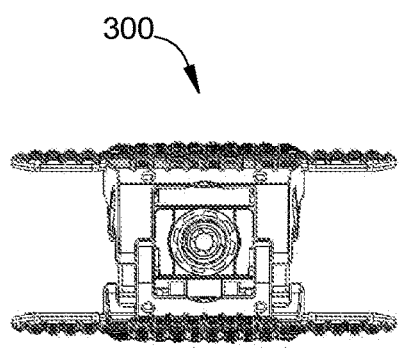
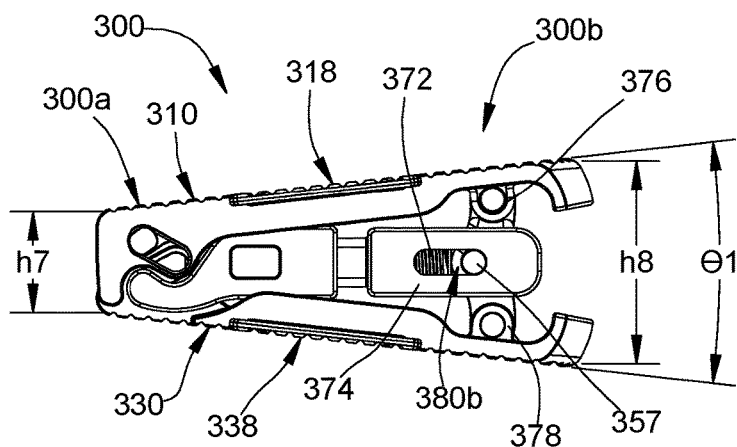
FIG. 25A  FIG. 25B
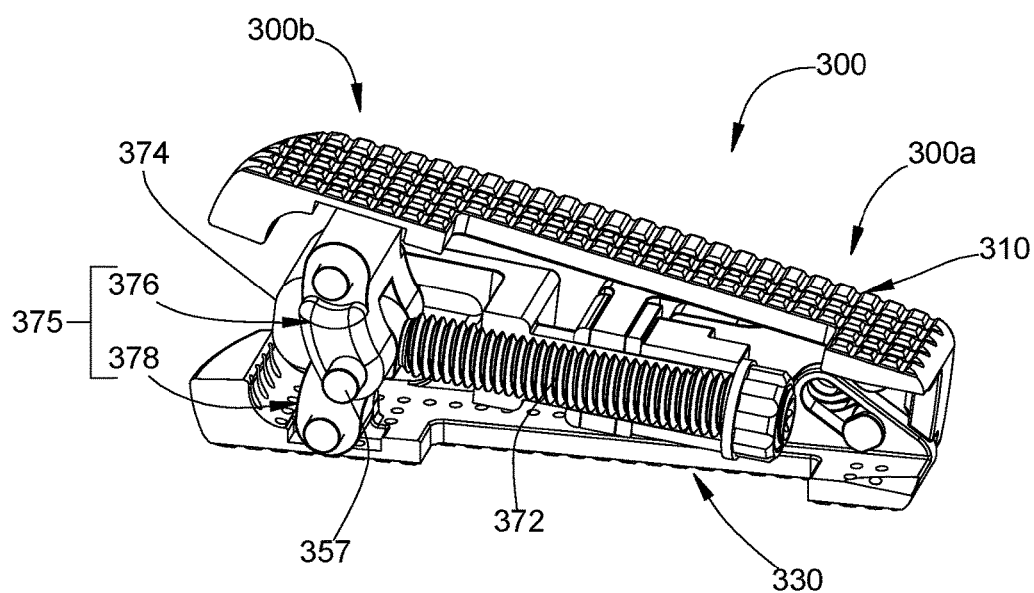
FIG. 25C

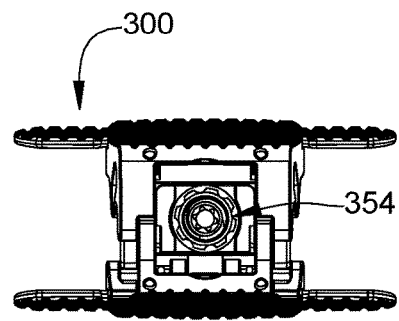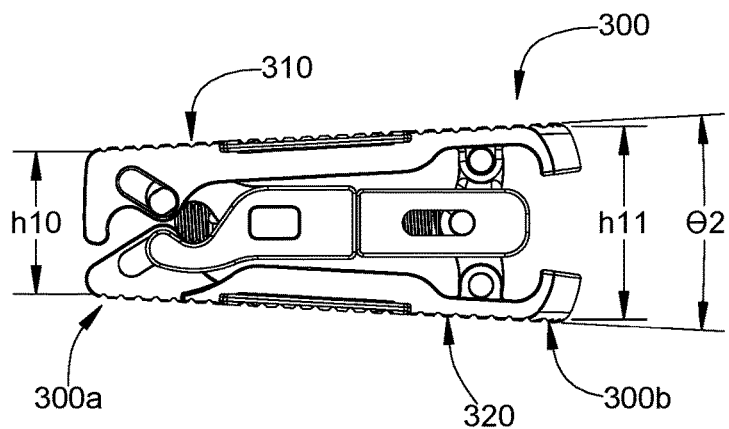
FIG. 27A  FIG. 27B
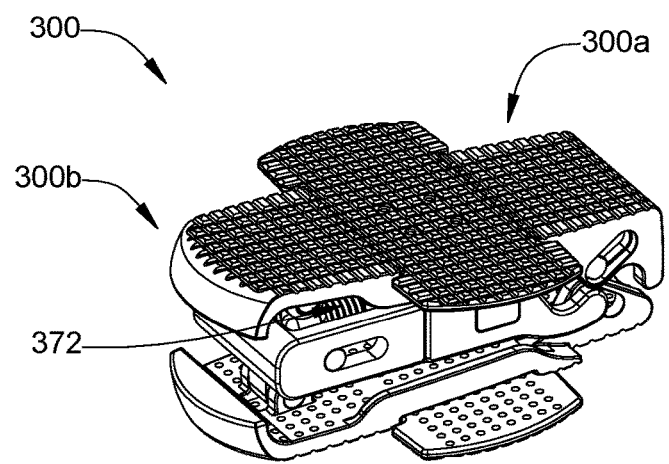
FIG. 27C

EXPANDABLE SPINAL IMPLANTS

CROSS-REFERENCE TO RELATED APPLICATIONS

This application is a continuation application of U.S. patent application Ser. No. 14/965,246, which was filed on Dec. 10, 2015, which claims the benefit of, and priority to, U.S. Provisional Patent Application Ser. No. 62/090,429, which was filed on Dec. 11, 2014, U.S. Provisional Patent Application Ser. No. 62/158,470, which was filed on May 7, 2015, and U.S. Provisional Patent Application Ser. No. 62/206,779, which was filed on Aug. 18, 2015, the entire contents of each of which are hereby incorporated herein by reference.

TECHNICAL FIELD

The present disclosure relates generally to orthopedic surgical devices, and more particularly, to expandable spinal implants configured for positioning within an intervertebral space, associated instrumentations, and methods of using the same.

BACKGROUND

The spinal column is a complex system of bones and connective tissues that provide support for the human body and protection for the spinal cord and nerves. The adult spine includes an upper portion and a lower portion. The upper portion contains twenty-four discrete bones, which are subdivided into three areas including seven cervical vertebrae, twelve thoracic vertebrae, and five lumbar vertebrae. The lower portion includes the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured disc, degenerative disc disease, vertebral body fracture, and tumors. Persons suffering from any of the above conditions typically experience extreme and/or debilitating pain, and often times diminished nerve function. These conditions and their treatments can be further complicated if the patient is suffering from osteoporosis, or bone tissue thinning and loss of bone density.

Spinal discs between the endplates of adjacent vertebrae in a spinal column of the human body provide critical support. However, due to injury, degradation, disease or the like, these discs can rupture, degenerate, and/or protrude to such a degree that the intervertebral space between adjacent vertebrae collapses as the disc loses at least a part of its support function. This can cause impingement of the nerve roots and severe pain.

In some cases, surgical correction may be required. Some surgical corrections include the removal of the natural spinal disc from between the adjacent vertebrae. In order to preserve the intervertebral disc space for proper spinal column function, an interbody spacer can be inserted between the adjacent vertebrae.

Typically, a prosthetic implant is inserted between the adjacent vertebrae and may include pathways that permit bone growth between the adjacent vertebrae until they are fused together. However, there exists a possibility that conventional prosthetic implants may be dislodged or moved from their desired implantation location due to movement by the patient before sufficient bone growth or fusion has occurred. Due to the concave nature of the vertebral body endplates, it can be challenging to obtain enough contact between the implant and the endplates to create bone growth. Additionally, achieving the desired lordosis can be difficult given the limitation of typical prosthetic implants once they are implanted.

Therefore, a need exists for a spinal implant that provides maximum contact with the vertebral body endplates, matches the desired amount of lordosis, allows for bone growth between adjacent vertebrae, maintains the space between adjacent vertebrae during bone ingrowth, and/or resists dislocation from its implantation site.

SUMMARY

In accordance with an aspect of the present disclosure, a spinal implant having a proximal region and a distal region includes an upper body, a lower body, a proximal adjustment assembly, and a distal adjustment assembly. Each of the upper and lower bodies includes an outer surface and an inner surface, and the inner surfaces of the upper and lower bodies are disposed in opposed relation relative to each other. The proximal adjustment assembly is disposed between the upper and lower bodies at the proximal region of the spinal implant and is adjustably coupled to the upper and lower bodies. The distal adjustment assembly is disposed between the upper and lower bodies at the distal region of the spinal implant and is adjustably coupled to the upper and lower bodies. The proximal and distal adjustment assemblies are independently movable to change a vertical height of at least one of the proximal region or the distal region of the spinal implant.

In embodiments, the proximal adjustment assembly includes a ramp slidably movable along the proximal region of the spinal implant to change the vertical height of the proximal region of the spinal implant. The ramp may include upper and lower rails that taper from a proximal end towards a distal end of the ramp. The distal end of the ramp may be disposed between the upper and lower bodies, and the ramp may be slidable between the upper and lower bodies to increase the vertical height of the proximal region of the spinal implant. Each of the upper and lower rails may include an inner surface, each of the inner surfaces of the upper and lower rails may include a plurality of grooves extending along a length thereof. The proximal adjustment assembly may further include a first set of pins coupled to the inner surface of the upper body and positioned against the inner surface of the upper rails, and a second set of pins coupled to the inner surface of the lower body and positioned against the inner surface of the lower rails. The first and second sets of pins may ride along the plurality of grooves of the upper and lower rails during movement of the ramp.

In embodiments, the distal adjustment assembly includes a pivot linkage assembly including an upper pivot linkage pivotably connected to the inner surface of the upper body, and a lower pivot linkage pivotable connected to the inner surface of the lower body. The upper and lower pivot linkages are pivotably connected to each other and movable with respect to each other to change the vertical height of the distal region of the spinal implant.

The distal adjustment assembly may include a curved plate having a curved distal surface movable into and out of contact with the pivot linkage assembly to effect movement of the upper and lower pivot linkages with respect to each other. The distal adjustment assembly may include a threaded post including a distal end retained against a proximal surface of the curved plate, wherein axial movement of the threaded post moves the curved plate. The distal adjustment assembly may include a bracket including a threaded opening and a pair of legs extending distally therefrom. The threaded post may be threadingly engaged with the threaded opening of the bracket and axially movable therethrough. The curved plate may be slidably disposed between the pair of legs of the bracket, and the upper and lower pivot linkages may be pivotable connected to each other by a pin extending through the upper and lower pivot linkages and a distal end of the pair of legs of the bracket.

The distal adjustment assembly may include a threaded post including a distal end movable into and out of contact with the pivot linkage assembly to effect movement of the upper and lower pivot linkages with respect to each other. The distal adjustment assembly may include an expander including a body portion defining a cavity therein and a distal end including a double ramped inner surface. The pivot linkage assembly may extend through the cavity of the expander such that pivot linkages contact the double ramped inner surface of the expander when moved by the threaded post. The expander may include a shaft extending proximally from the body portion. The shaft may include a threaded opening defined therein, and the threaded post may be threadingly engaged with the threaded opening of the shaft and axially movable therethrough into the cavity of the expander.

In embodiments, each of the inner surfaces of the upper and lower bodies includes a pair of proximal fins defining angled slots therethrough, and the proximal adjustment assembly includes a linkage body and a first set of pins. The linkage body includes a pair of arms extending along lateral sides thereof, and each arm of the pair of arms includes a distal hole. The first set of pins is disposed within the distal holes of the linkage body and into the angled slots of the upper and lower bodies. Movement of the linkage body causes the first set of pins to translate within the angled slots to change the vertical height of the proximal region of the spinal implant.

The proximal adjustment assembly may include a flange nut having a threaded opening defined therethrough that is threadingly engaged with the threaded post of the distal adjustment assembly. The linkage body may include a recess in which a distal flange of the flange nut is disposed, such that axial movement of the flange nut along the threaded post effects movement of the linkage body. The pair of proximal fins of the upper and lower bodies may define vertical slots therethrough. The proximal adjustment assembly may include a coupler that includes a pair of nubs extending from lateral sides thereof that is slidably disposed within the vertical slots of the upper and lower bodies.

In embodiments, the side surfaces of the upper and lower bodies may include angled slots defined therethrough, and the proximal adjustment assembly may include a bracket assembly including a plurality of nubs slidably disposed within the angled slots of the upper and lower bodies, such that movement of the bracket assembly causes the plurality of nubs to translate within the angled slots to change the vertical height of the proximal region of the spinal implant.

The proximal adjustment assembly may include a nut having a threaded opening defined therethrough that is threadingly engaged with the threaded post of the distal adjustment assembly, such that axial movement of the nut along the threaded post effects movement of the bracket assembly.

At least one of the outer surfaces of the upper and lower bodies may include a wing portion that is movable from a retracted position in which the wing portion is aligned with the outer surface of the upper body or the lower body, and a deployed position in which the wing portion is rotated at an angle relative to the outer surface of the upper body or the lower body. At least one of the outer surfaces of the upper body or the lower body may include a plurality of retaining features.

In accordance with another aspect of the present disclosure, a method of spacing vertebral bodies includes: implanting a spinal implant into a disc space defined between first and second endplates of respective first and second vertebral bodies such that an upper body of the spinal implant is adjacent the first end plate and a lower body of the spinal implant, disposed in opposed relation relative to the upper body, is adjacent the second end plate, the spinal implant including proximal and distal adjustment assemblies disposed between the upper and lower bodies, the proximal and distal adjustment assemblies independently and adjustably coupled to proximal and distal regions, respectively, of the spinal implant; and adjusting a vertical height of at least one of the proximal region or the distal region of the spinal implant via one of the proximal or distal adjustment assemblies such that at least one of the outer surfaces of the upper or lower bodies of the spinal implant matches an anatomical shape of the first or second endplates of the first or second vertebral bodies.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 1 is a perspective view of a spinal implant in accordance with an embodiment of the present disclosure;

FIG. 2 is an exploded view of the spinal implant of FIG. 1;

FIGS. 4A and 4B are perspective views of the spinal implant of FIG. 1, in a collapsed position;

FIG. 4C-4E are side, end, and cross-sectional views, respectively, of the spinal implant of FIGS. 4A and 4B;

FIGS. 9A and 9B are perspective views of the spinal implant of FIG. 1, with a proximal region of the spinal implant in a fully expanded position and a distal region of the spinal implant in a partially expanded position;

FIGS. 10A and 10B are perspective views of the spinal implant of FIG. 1, with proximal and distal regions of the spinal implant each in a fully expanded position;

FIGS. 11A-11E are perspective views of a system including the spinal implant of FIG. 1 and an insertion instrument in accordance with an embodiment of the present disclosure;

FIG. 11F is a close-up view of the area of detail indicated in FIG. 11E;

FIG. 11G is a perspective view of the area of detail of the system of FIG. 11F;

FIGS. 11H and 11I are perspective views of the system of FIGS. 11A-11E;

FIG. 11J is a close-up view of the area of detail indicated in FIG. 11I;

FIGS. 12A and 12B are perspective views of a spinal implant in accordance with another embodiment of the present disclosure;

FIG. 13 is an exploded view of the spinal implant of FIGS. 12A and 12B;

FIGS. 18A-18E are perspective views of a system including the spinal implant of FIGS. 12A-12B and an insertion instrument in accordance with an embodiment of the present disclosure;

FIGS. 25A-25C are end, side, and cut-away views, respectively, of the spinal implant of FIG. 19, with a distal region of the spinal implant in a fully expanded position;

FIGS. 27A-27C are end, side, and perspective views, respectively, of the spinal implant of FIG. 19, with proximal and distal regions of the spinal implant each in a fully expanded position.

DETAILED DESCRIPTION

Figure 3A:
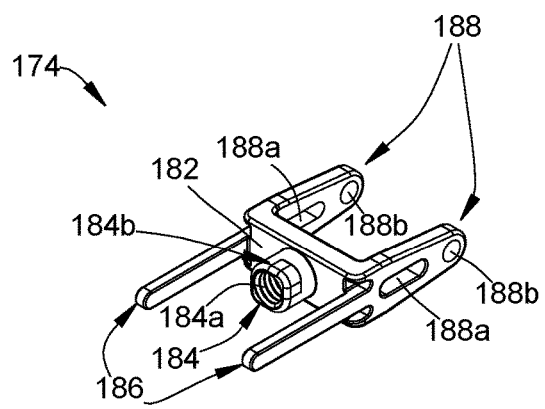
FIGS. 3A and 3B are perspective views of a bracket of the spinal implant of FIGS. 1 and 2.
Figure 3B:
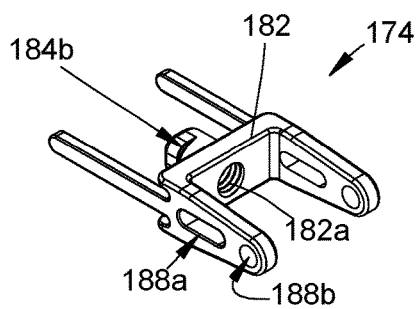
Figure 3C:
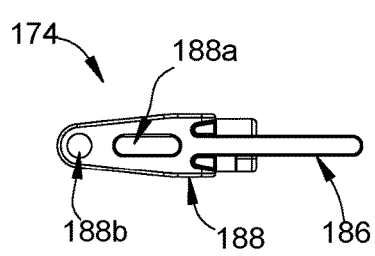
FIG. 3C-3E are side, end, and cross-sectional views, respectively, of the bracket of FIGS. 3A and 3B.
Figure 3D:
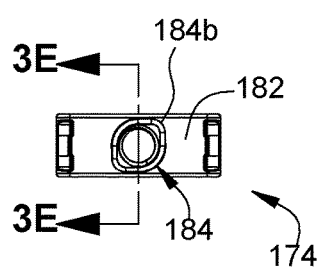
Figure 3E:
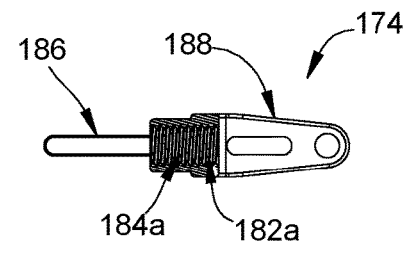

Embodiments of the present disclosure are now described in detail with reference to the drawings in which like reference numerals designate identical or corresponding elements in each of the several views. The term "clinician" refers to a doctor (e.g., a surgeon), a nurse, or any other care provider, and may include support personnel. Throughout this description, the term "proximal" refers to a portion of a device or component thereof that is closer to a clinician, and the term "distal" refers to the portion of the device or component thereof that is farther from the clinician.

Referring now to the drawings, FIG. 1 illustrates an expandable spinal implant or a spinal implant 100 in accordance with an embodiment of the present disclosure. Spinal implant 100 has a proximal region 100a and a distal region 100b extending along a longitudinal axis "X." The spinal implant 100 includes an upper body 110 and a lower body 130 disposed in opposed relation relative to each other and coupled together by a proximal adjustment assembly 150 and a distal adjustment assembly 170. The proximal and distal adjustment assemblies 150, 170 are independently movable to allow for adjustment in the distance between the upper and lower bodies 110, 130 of the proximal and distal regions 100a, 100b of the spinal implant 100 along a transverse axis "Y." Accordingly, the spinal implant 100 is movable between a collapsed position and a fully expanded position, and includes a number of partially expanded positions, as described in further detail below.

Turning now to FIG. 2, the upper body 110 of the spinal implant 100 includes an elongated substantially planar portion 112 having a proximal end 112a and a distal end 112b, and a curved portion 114 disposed distally of the distal end 112b of the planar portion 112. An outer surface 116 of the planar portion 112 includes a plurality of retaining features 116a configured to frictionally engage an adjacent surface of a vertebral body (i.e., a vertebral endplate) to maintain the position of the spinal implant 100 relative to the vertebral body and to inhibit the spinal implant 100 from backing out of the intervertebral space as the plurality of retaining features 116 may bite into the vertebral endplate. The plurality of retaining features may be ridges, protrusions, bumps, teeth, or any other texturized structure, as is within the purview of those skilled in the art.

An inner surface 118 of the upper body 110 includes two pairs of proximal posts 120 extending from the proximal end 112a of the planar portion 112. Each proximal post 120 includes a through hole 120a defined therethrough that is aligned with the through holes 120a of the other proximal posts 120. The inner surface 118 of the upper body 110 also includes a pair of distal posts 122 extending from the distal end 112b of the planar portion 112, proximate to the curved portion 114. Each distal post 122 include a through hole 122a defined therethrough. It should be understood that the proximal and distal posts 122 that are not shown are identical to the proximal and distal posts 122 shown, and similar to the proximal and distal posts 140 and 142 of the lower body 130.

The lower body 130 includes an elongated substantially planar portion 132 having a proximal end 132a and a distal end 132b, and a curved portion 134 disposed distally of the distal end 132b of the planar portion 132. The planar portion 132 includes an outer surface 136 having a plurality of retaining features (not shown) disposed thereon that are configured to frictionally engage an adjacent surface of a vertebral body as discussed above with regard to the plurality of retaining features 116a of the upper body 110. An inner surface 138 of the lower body 130 includes two pairs of proximal posts 140 extending from the proximal end 132a of the planar portion 132. Each proximal post 140 includes a through hole 140a defined therethrough that is aligned with the through holes 140a of the other proximal posts 140. The inner surface 138 of the lower body 130 also includes a pair of distal posts 142 extending from the distal end 132b of the planar portion 132, proximate to the curved portion 134. Each distal post 142 includes a through hole 142a defined therethrough.

The proximal adjustment assembly 150 includes a ramp 152 having a proximal wall 154 at a proximal end 152a of the ramp 152. The proximal wall 154 includes a central opening 154a (see e.g., FIG. 4A) defined therethrough. A pair of upper rails 156 and a pair of lower rails 158 extend distally from the proximal wall 154 towards a distal end 152b of the ramp 152. The upper and lower rails 156, 158 are inclined and taper from the proximal end 152a to the distal end 152b of the ramp 152 such that when viewed from the side, the ramp 132 defines a wedge shape. The distal end 152b of the ramp 152 includes a pair of opposed guides 160 that are configured to engage arms 186 of a bracket 174 of the distal adjustment assembly 170, and be guided thereal-ong.

Each upper rail 156 includes an outer surface 162 and an inner surface 164, and each lower rail 158 includes an outer surface 166 and an inner surface 168. The outer surfaces 162, 166 of the upper and lower rails 156, 158 face the inner surfaces 118, 138 of the upper and lower bodies 110, 130 and are configured to slide relative thereto. The inner surfaces 164, 168 of the upper and lower rails 156, 158 are disposed in opposed and tapering spaced relation relative to each other. A plurality of grooves 169 extend along each of the inner surfaces 164, 168 of the upper and lower rails 156, 158. The plurality of grooves 169 may be a plurality of recesses, indentations, depressions, or the like for providing the inner surfaces 164, 168 of the upper and lower rails 156, 158 with an undulating surface.

Each upper rail 156 is received between a pair of the proximal posts 120 of the upper body 110 such that the through holes 120a of the proximal posts 120 are aligned with a groove 169 of the plurality of grooves 169 extending along the inner surface 164 of the upper rails 158. A first set of pins 151 respectively extends through and frictionally engages a pair of the proximal posts 120 and one groove 169 of the upper rails 158 to couple the upper body 110 to the ramp 152. Similarly, each lower rail 158 is received between a pair of the distal posts 140 of the lower body 130 such that through holes 140a of the distal posts 140 are aligned with a groove 169 of the plurality of grooves 169 extending along the inner surface 168 of the lower rail 158. A second set of pins 153 respectively extends through and frictionally engages a pair of the distal posts 140 and the groove 169 of the lower rails 158 to couple the lower body 130 to the ramp 152.

The first and second set of pins 151, 153 are configured to ride along the plurality of grooves 169 of respective upper and lower rails 156, 158 of the ramp 152 as the ramp 152 is moved proximally and/or distally with respect to the upper and lower bodies 110, 130. Accordingly, the ramp 152 is mechanically coupled to the upper and lower bodies 110, 130 and movable into and out of a space disposed between the upper and lower bodies 110, 130 to change the distance between the upper and lower bodies 110 and 130, and thus, the angular position and the vertical height of the spinal implant 100 about the proximal region 100a of the spinal implant 100.

The distal adjustment assembly 170 includes a threaded post or screw 172, a bracket 174, a curved plate 176, and a pivot linkage assembly 177 including an upper pivot linkage 178 and a lower pivot linkage 180. The threaded post 172 includes an elongated threaded body 172a having a proximal end 172b configured to mate with a driver 15 of an insertion instrument 10 (see e.g., FIG. 11H) and a flanged distal end 172c coupled to the curved plate 176. The proximal end 172b of the threaded post 172 may have a shape, such as a hex shape (not shown) for mating with the insertion instrument.

As shown in FIGS. 3A-3E, in conjunction with FIG. 2, the bracket 174 includes a base plate 182 defining a threaded opening 182a therethrough, and a boss 184 extending proximally from the base plate 182 and having a threaded opening 184a that is coterminous with the threaded opening 182a of the base plate 182. The threaded openings 182a and 184a of the base plate 182 and the boss 184 are configured to threadingly engage the threaded post 172 such that rotation of the threaded post 172 results in axial movement of the threaded post 172 through the bracket 174. The boss 184 includes a partially flanged proximal end 184b for connection with an insertion instrument 10 (see e.g., FIG. 11A). The bracket 174 also includes a pair of arms 186 extending proximally from the base plate 182 that is configured to guide the ramp 152, and a pair of legs 188 extending distally from the base plate 182. The pair of legs 188 includes opposed longitudinal slots 188a and opposed holes 188b. The opposed holes 188b are disposed distally of the longitudinal slots 188a.

Figure 10C:
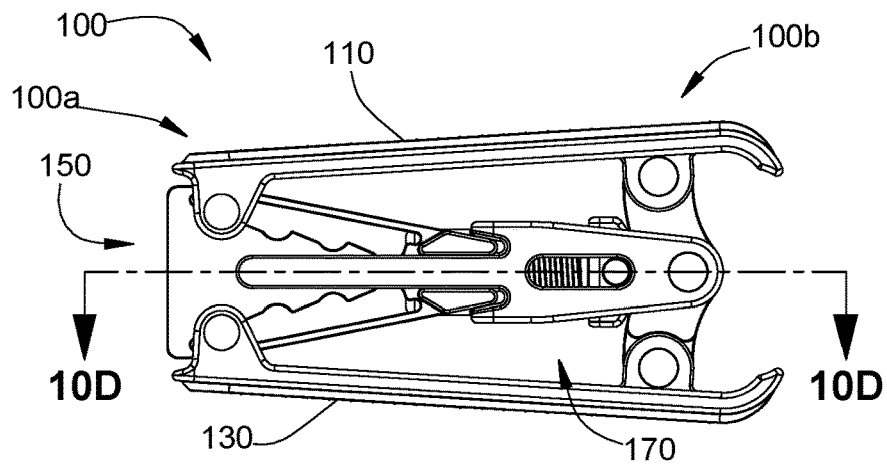
FIG. 10C is a side view of the spinal implant of FIGS. 10A and 10B.
Figure 10D:
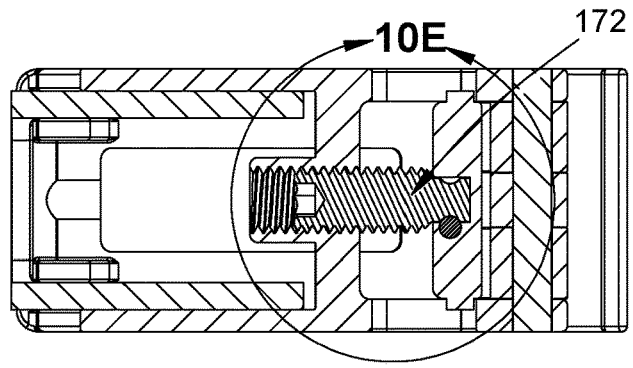
FIG. 10D is a cross-sectional view of the spinal implant of FIGS. 10A-10C, taken along line 10D-10D of FIG. 10C.
Figure 10E:
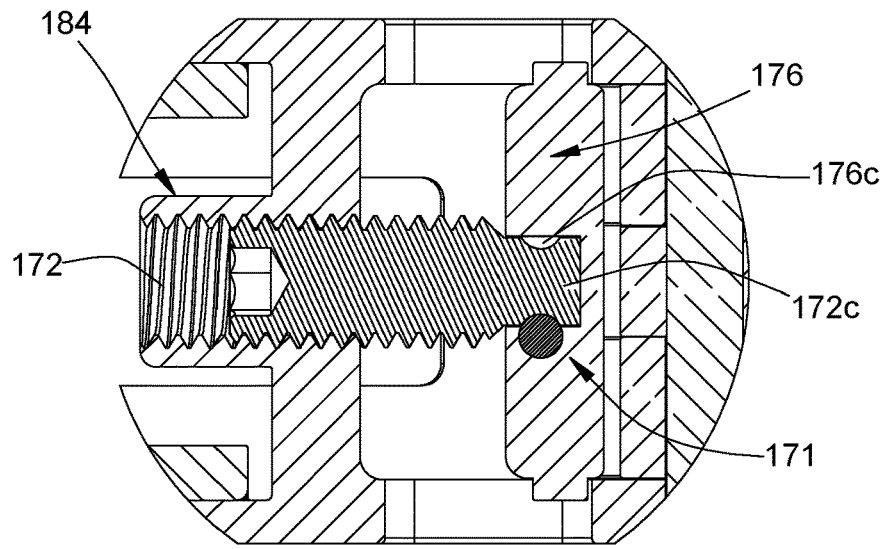
FIG. 10E is a close-up view of the area of detail indicated in FIG. 10D.

Referring again to FIG. 2, the curved plate 176 includes a curved distal surface 176a and a proximal surface 176b having a cavity 176c defined therein (FIG. 10E) that is aligned with and configured to receive and retain the flanged distal end 172c of the threaded post 172 therein via a pin 171. A pair of nubs 190 extends laterally from sides of the curved plate 176 and is disposed, and longitudinally movable, within the longitudinal slots 188a of the legs 188 of the bracket 174.

The pivot linkage assembly 177 includes an upper pivot linkage 178 having an upper hole 178a and a lower hole 178b, and a lower pivot linkage 180 having a pair of upper holes 180a and a lower hole 180b. The upper hole 178a of the upper pivot linkage 178 is aligned with the through holes 122a defined in the distal posts 122 of the upper body 110, and a pin 155 is inserted therethrough for pivotably connecting the upper pivot linkage 178 with the upper body 110. The lower hole 180b of the lower pivot linkage 180 is aligned with the through holes 142a defined in the distal posts 142 of the lower body 130, and a pair of pins 157 are inserted therethrough for pivotably connecting the lower pivot linkage 180 with the lower body 130. The lower hole 178b of the upper pivot linkage 178 and the upper holes 180a of the lower pivot linkage 180 are aligned with the holes 188b in the legs 188 of the bracket 174, and a pin 159 is disposed therethrough for pivotably securing the upper and lower bodies 110 and 130 to the bracket 174 via the upper and lower pivot linkages 178, 180.

Accordingly, the upper and lower pivot linkages 178, 180 are coupled to the upper and lower bodies 110, 130, and are pivotable relative to each other about the pin 159 to change the distance between the upper and lower bodies 110, 130, and thus, the angular position and vertical height of the spinal implant 100 about the distal region 100b of the spinal implant 100. Thus, the proximal and distal regions 100a and 100b of the spinal implant 100 are independently movable with respect to each other via the proximal and distal adjustment assemblies 150, 170 so that the spinal implant 100 may have a variety of configurations.

The independent adjustability of the proximal and distal regions 100a, 100b of the spinal implant 100 allows a clinician to adjust the dimensions of the spinal implant 100 (i.e., vertical heights of the proximal and distal regions) such that the spinal implant 100 can be inserted between two vertebrae with relatively narrow access in the collapsed position, without force, to avoid trauma to the vertebral bodies, and in particular, the endplates of the vertebral bodies. The proximal and/or distal regions 100a, 100b of the spinal implant 100 can then be adjusted to partially or fully expanded positions so that the upper and lower bodies 110, 130 are aligned with the endplates to maximize surface contact between the spinal implant 100 and the endplates, and to match the dimensions of the disc space defined between the endplates in which the spinal implant 100 is disposed. The adjustability of the spinal implant 100 allows a clinician, for example, to minimize trauma to the vertebrae during implantation of the spinal implant 100, to tailor the spinal implant 100 to conform to the anatomy of individual patients, to maximize contact between the spinal implant 100 and the endplates to create bone growth, to match the natural disc height of the disc space, to improve the seating of the spinal implant 100 within the disc space, and/or to lessen the likelihood of expulsion of the spinal implant 100 from the disc space.

As shown in FIGS. 4A-4E, the spinal implant 100 has a collapsed, or unexpanded, position. In the collapsed position, planar portions 112, 132 of the upper and lower bodies 110, 130 are disposed in parallel relationship to each other. Each of the proximal and distal regions 100a, 100b of the spinal implant 100 has a height, "h1," that defines the minimum distance at which the upper and lower bodies 110, 130 may be positioned relative to each other. In embodiments, height, "h1," may range from about 2 mm to about 12 mm. The ramp 152 is disposed in a proximalmost position such that the first and second set of pins 151 and 153 are engaged with the distalmost groove of the plurality of grooves 169, and the curved plate 176 is disposed in a proximalmost position with the nubs 190 of the curved plate 176 disposed in a proximalmost part of the longitudinal slots 188a of the bracket 174 such that the upper and lower pivot linkages 178, 180 are in the collapsed position.

Figure 5A:
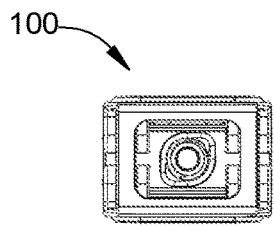
FIGS. 5A and 5B are end and side views, respectively, of the spinal implant of FIG. 1, with a proximal region of the spinal implant in a partially expanded position.
Figure 5B:
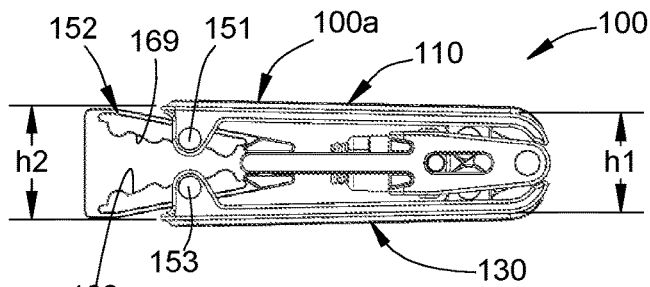
Figure 6A:
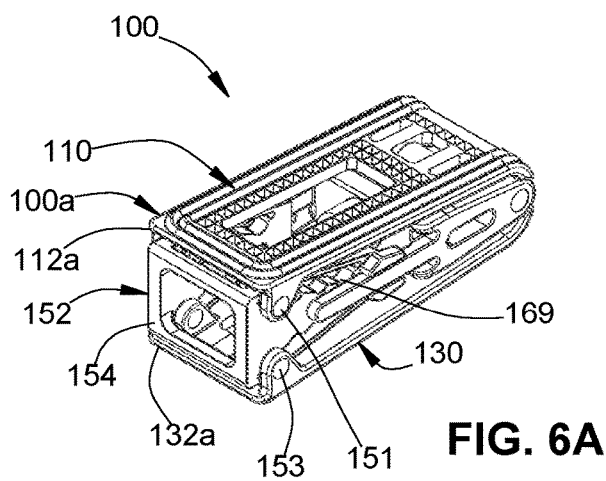
FIGS. 6A and 6B are perspective views of the spinal implant of FIG. 1, with a proximal region of the spinal implant in a fully expanded position.
Figure 6B:
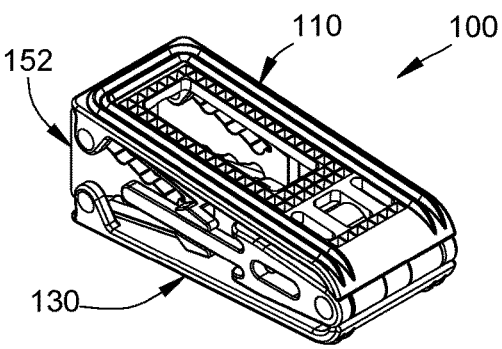
Figure 6C:
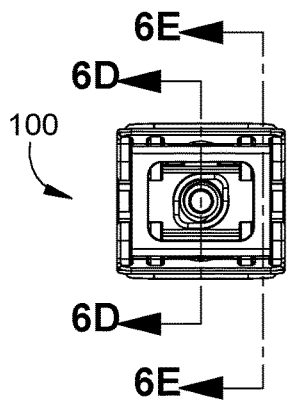
FIG. 6C is an end view of the spinal implant of FIGS. 6A and 6B.
Figure 6D:
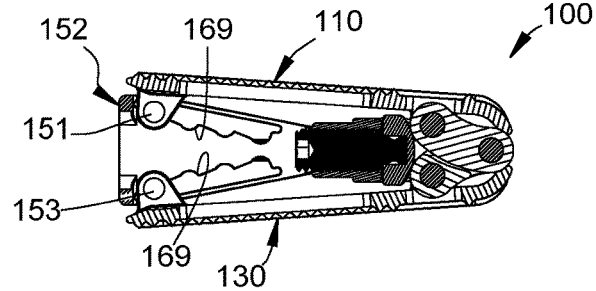
FIGS. 6D and 6E are cross-sectional views of the spinal implant of FIGS. 6A-6C, taken along lines 6D-6D and 6E-6E, respectively, of FIG. 6C.
Figure 6E:
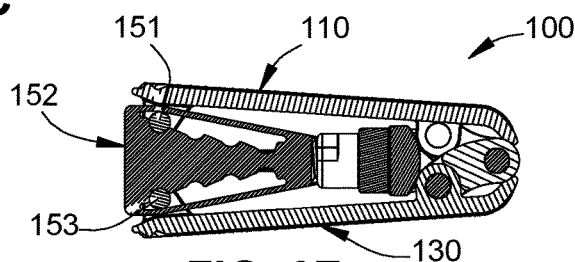

The ramp 152 of the proximal adjustment assembly 150 may be advanced distally between the upper and lower bodies 110, 130 to drive the upper and lower bodies 110, 130 apart at the proximal region 100a of the spinal implant 100. As shown in FIGS. 5A-5B, the ramp 152 may be moved distally such that the first and second set of pins 151, 153 are moved to a groove in the plurality of grooves 169 adjacent to the distalmost groove of the embodiment of FIGS. 4A-4E to partially expand the proximal region 100a of the spinal implant 100 to a height, "h2," to provide the spinal implant 100 with a kyphotic shape. In embodiments, the height, "h2," may range from about 3 mm to about 13 mm. In some embodiments, each groove 169 provides 1 mm of expansion at the proximal region 100a of the spinal implant 100. However, it should be understood that the grooves 169 may be configured to provide different amounts of expansion based on the size and number of grooves provided in the upper and lower rails 156, 158 of the ramp 152. For example, each groove 169 may provide more or less than 1 mm of expansion and the amount of expansion for each groove 169 may not be uniform along the upper and lower rails 156, 158. As shown in FIGS. 6A-6E, the ramp 152 may be fully advanced such that the first and second set of pins 151, 153 are moved into a proximalmost groove of the plurality of grooves 169 to achieve maximum expansion at the proximal region 100a of the spinal implant 100. When fully advanced, the proximal wall 154 of the ramp 152 is flush with the proximal ends 112a, 132a of the upper and lower bodies 110, 130.

The distal adjustment assembly 170 can be actuated by driving the threaded post 172 distally through the threaded openings 184a, 182a of the boss 174 and base plate 182 of the bracket 174 to push the curved plate 176 against the upper and lower pivot linkages 178, 80 to move the upper and lower pivot linkages 178, 180 apart. Thus, movement of the curved plate 176 controls the displacement of the upper and lower pivot linkages 178, 180 relative to each other.

Figure 7A:
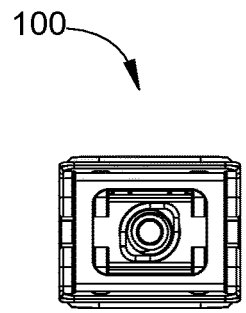
FIGS. 7A and 7B are end and side views, respectively, of the spinal implant of FIG. 1, with proximal and distal regions of the spinal implant each in a partially expanded position.
Figure 7B:
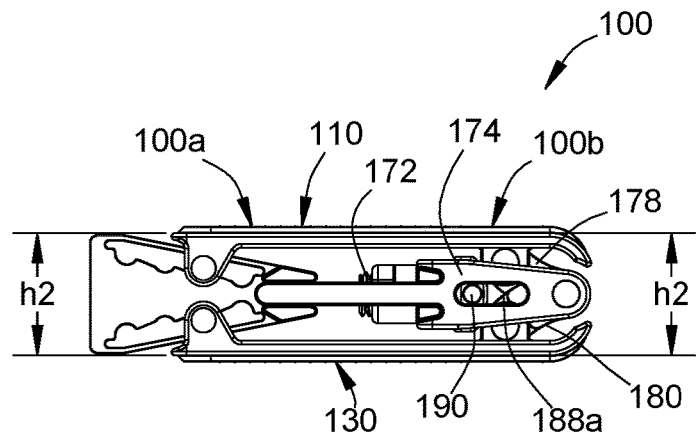
Figure 8A:
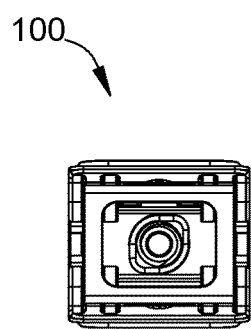
FIGS. 8A and 8B are end and side views, respectively, of the spinal implant of FIG. 1, with a proximal region of the spinal implant in a partially expanded position and a distal region of the spinal implant in a fully expanded position.
Figure 8B:
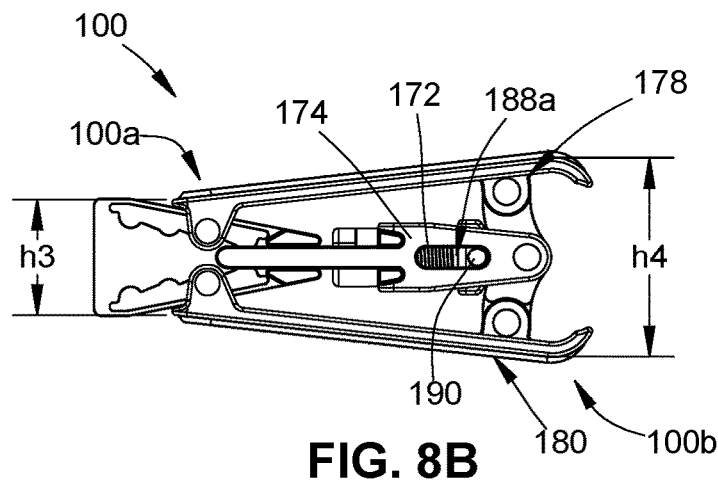

As shown in FIGS. 7A-7B, with the proximal region 100a of the spinal implant 100 in the partially expanded position of FIGS. 5A-5B, rotation of the threaded post 172 in a first direction moves the threaded post 172 distally which in turn, pushes the curved plate 176 (see e.g., FIG. 10E) distally such that the nubs 190 of the curved plate move distally within the longitudinal slots 188a of the bracket 174 and the curved distal surface 176a of the curved plate 176 (FIG. 2) pushes against the upper and lower pivot linkages 178 and 180 to change the distance between the upper and lower bodies 110, 130 in the distal region 100b of the spinal implant 100. The distal region 100b of the spinal implant 100 may be adjusted to have the same height, "h2," as the proximal region 100a of the spinal implant 100 such that the upper and lower bodies 110, 130 are parallel to each other. As shown in FIGS. 8A-8B, with the proximal region 100a of the spinal implant in a partially expanded position having a height, "h3," the threaded post 172 may be fully advanced such that the nubs 190 of the curved plate 176 are disposed in a distalmost portion of the longitudinal slots 188a of the bracket 174 to achieve maximum expansion at the distal region 100b, to a height, "h4," of the spinal implant 100. In embodiments, the height, "h3," may range from about 3 mm to about 13 mm, and the height, "h4," may range from about 8 mm to about 18 mm.

As shown in FIGS. 9A-9B, with the proximal region 100a of the spinal implant 100 in the fully expanded position, as previously illustrated in FIGS. 6A-6E, the threaded post 172 is moved a distance axially such that the distal region 100b of the spinal implant 100 is adjusted to have the same height as the proximal region 100a of the spinal implant 100. As shown in FIGS. 10A-10E, the distal adjustment assembly 170 is shown in a fully expanded position to achieve maximum expansion of both the proximal and distal regions 100a, 100b of the spinal implant 100.

A person of ordinary skill in the art will readily understand that the proximal and distal regions of the spinal implant may be independently adjusted to achieve a desired configuration of the spinal implant. Accordingly, it is contemplated that only the proximal region or the distal region of the spinal implant may be expanded, should that be a desired configuration, or both the proximal and distal regions of the spinal implant may be expanded to achieve a desired configuration (e.g., an implant having a kyphotic shape, a lordotic shape, etc.).

Figure 11A:
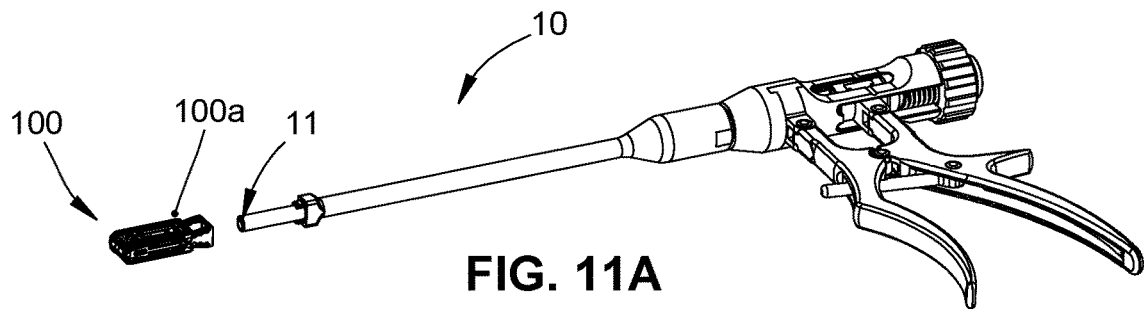
Figure 11B:
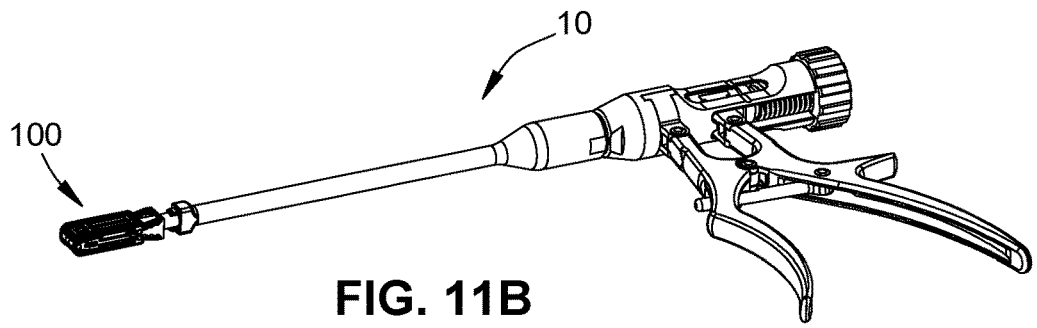
Figure 11C:
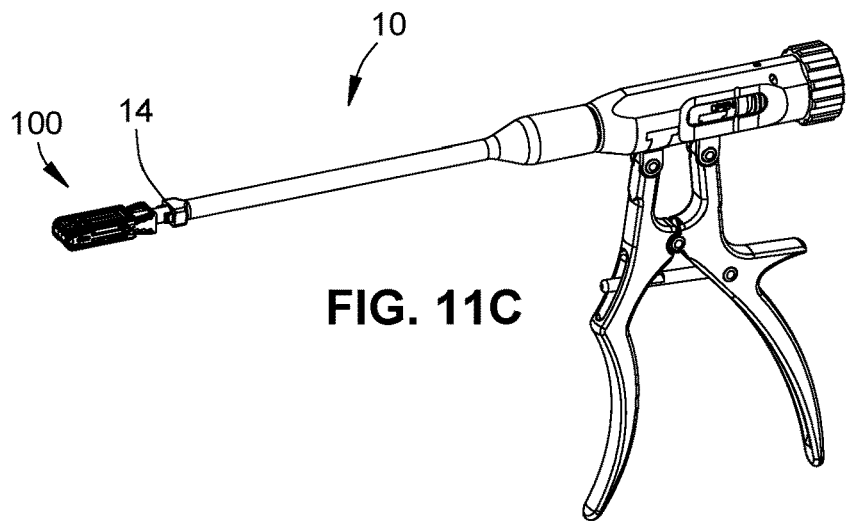
Figure 11D:
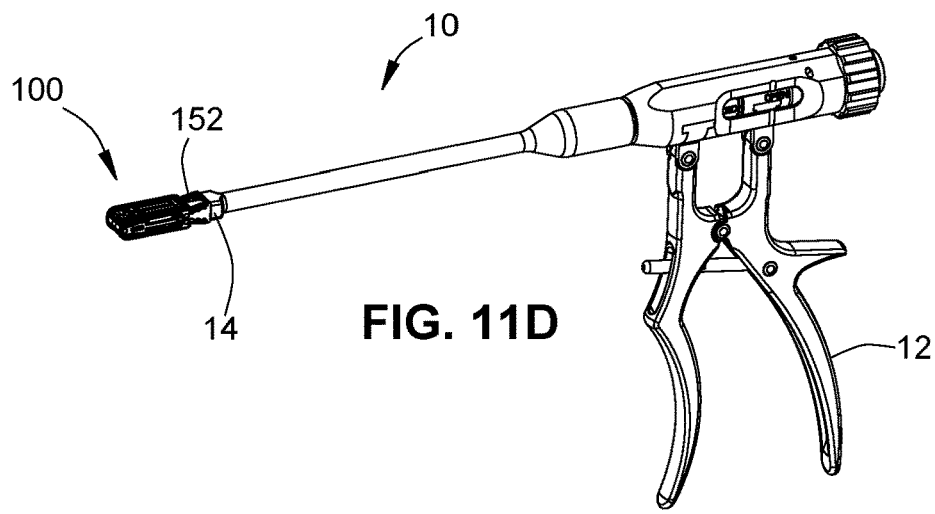

Referring now to FIGS. 11A-11J, a method for inserting, positioning, and/or adjusting (e.g., expanding) the spinal implant 100 in an interdisc space between adjacent vertebral bodies with an insertion instrument 10 is shown. As shown in FIG. 11A, a tip 11 of the insertion instrument 10 is aligned with the proximal region 100a of the spinal implant 100 disposed in the collapsed position. As shown in FIG. 11B, the tip 11 of the insertion instrument 10 is placed into the spinal implant 100 through the central opening 154a of the proximal wall 154 of the ramp 152, between the upper and lower bodies 110 and 130 of the spinal implant 100, and over the boss 184 of the bracket 174 (see e.g., FIG. 2). As shown in FIG. 11C, the insertion instrument 10 is rotated 90 degrees so that the tip 11 engages the partially flanged proximal end 184b of the boss 184 (see e.g., FIG. 3D) for releasable attachment of the insertion instrument 10 to the spinal implant 100. As shown in FIGS. 11D-11E, handles 12 of the insertion instrument 10 may be squeezed and/or a thumb wheel 13 of the insertion instrument 10 may be rotated to advance the tip 11 of the insertion instrument 10 distally into the ramp 152 such that a flanged portion 14 of the insertion instrument 10 abuts the proximal wall 154 of the ramp 152 to push the ramp 152 between the upper and lower bodies 110 and 130 and thus, expand the proximal region 100a of the spinal implant 100 as shown in FIGS. 11F and 11G.

As shown in FIG. 11H, a driver 15 is inserted through the insertion instrument 10 and includes a shaped distal end 16 configured to engage the proximal end 172b of the threaded post 172 (see e.g., FIG. 2) of the spinal implant 100. As shown in FIG. 11I, as the driver 15 is rotated, the threaded post 172 is also rotated and moved distally against the curved plate 176 thereby moving the curved plate 176 into the upper and lower pivot linkages 178 and 180 (see e.g., FIG. 2) to expand the distal region 100b of the spinal implant 100, as shown in FIG. 11J.

While shown fully expanded, it should be understood that the insertion instrument 10 may be advanced and/or the driver 15 may be rotated to expand the proximal and/or distal regions 100a, 100b of the spinal implant 100 to any desired position.

In use, a clinician removes all or a portion of a disc from between two vertebral bodies (e.g., complete or partial diskectomy), and scrapes and cleans the endplates of the vertebral bodies to prepare the surfaces for placement of the spinal implant 100 such that a fusion will occur. Next, the clinician places the spinal implant 100 into the disc space using the insertion instrument 10. The insertion instrument 10 is attached to the implant by inserting the tip 11 of the insertion instrument 10 over the boss 184 of the bracket 174 and rotating the insertion instrument 10 ninety (90) degrees to engage the partially flanged proximal end 184b of the boss 184, as described above. The insertion instrument 10 may be pre-attached to the spinal implant 100 prior to inserting the spinal implant 100 into the disc space, or may be attached after the spinal implant 100 is positioned in the disc space. The handles 12 and/or the thumb wheel 13 of the insertion instrument 10 is actuated to drive the ramp 152 distally into the spinal implant 100 and thus increase the proximal height of the spinal implant 100 in discrete increments (e.g., 1 mm increments) as the first and second set of pins 151, 153 advance distally into grooves 169 of the respective upper and lower rails 156, 158. With the driver 15 inserted through the insertion instrument 10 to engage threaded post 172, rotation of the driver 15 in a first direction (e.g., clockwise) drives the threaded post 172 distally against the curved plate 176 to expand the upper and lower pivot linkages 178, 180 and thus, increase the distal height of the spinal implant 100.

Various allograft and/or autograft materials may be placed into and/or next to the spinal implant 100 to assist in the fusion process. Should the clinician need to adjust the distal height of the implant 100 once it is expanded, the driver 15 would be re-engaged with the threaded post 172 and rotated in a second direction (e.g., counter-clockwise) to drive the threaded post 172 proximally. Should the proximal height need to be adjusted, a separate instrument (not shown) would be utilized to move the upper and lower bodies 110 and 130 away from the ramp 152.

Referring now to FIGS. 12A and 12B, an expandable spinal implant or spinal implant 200 in accordance with another embodiment of the present disclosure is shown. The spinal implant 200 is similar to the spinal implant 100 and therefore will be described with respect to the differences therebetween.

The spinal implant 200 has a proximal region 200a and a distal region 200b, and includes an upper body 210 and a lower body 230 disposed in opposed relation relative to each other and coupled together by a proximal adjustment assembly 250 and a distal adjustment assembly 270. The proximal and distal adjustment assemblies 250 and 270 are independently movable to allow for adjustment in the angular and vertical distance between the upper and lower bodies 210, 230 of the proximal and distal regions 200a, 200b of the spinal implant 200.

The independent adjustability of the proximal and distal regions 200a, 200b of the spinal implant 200 allows a clinician to adjust the dimensions of the spinal implant 200 (i.e., vertical heights of the proximal and distal regions) such that the spinal implant 200 can be inserted between two vertebrae with relatively narrow access in the collapsed position, without force, to avoid trauma to the vertebral bodies, and in particular, the endplates of the vertebral bodies. The proximal and/or distal regions 200a, 200b of the spinal implant 200 can then be adjusted to partially or fully expanded positions so that the upper and lower bodies 210, 230 are aligned with the endplates to maximize surface contact between the spinal implant 200 and the endplates, and to match the dimensions of the disc space defined between the endplates of the vertebral bodies in which the spinal implant 200 is disposed. The adjustability of the spinal implant 200 allows a clinician, for example, to minimize trauma to the vertebrae during implantation of the spinal implant 200, to tailor the spinal implant 200 to conform to the anatomy of individual patients, to maximize contact between the spinal implant 200 and the endplates to create bone growth, to match the natural disc height of the disc space, to improve the seating of the spinal implant 200 within the disc space, and/or to lessen the likelihood of expulsion of the spinal implant 200 from the disc space.

Turning now to FIG. 13, the upper body 210 of the spinal implant 200 includes an elongated substantially planar portion 212 and a curved portion 214 disposed distally of the planar portion 212. An outer surface 216 of the planar portion 212 includes a plurality of retaining features 216a. An inner surface 218 of the upper body 210 includes a pair of proximal fins 220 and a pair of distal posts 222. Each proximal fin 220 includes an angled slot 220a and a vertical slot 220b defined therein. The angled slot 220a is disposed proximal to the vertical slot 220b. Each distal post 222 includes a through hole 222a defined therethrough.

The lower body 230 includes an elongated substantially planar portion 232 and a curved portion 234 disposed distally of the planar portion 232. The planar portion 232 includes an outer surface 236 having a plurality of retaining features 236a disposed thereon. An inner surface 238 of the lower body 230 includes a pair of proximal fins 240 and a pair of distal posts 242. Each proximal fin 240 includes an angled slot 240a and a vertical slot 240b defined therein. Each distal post 242 includes a through hole 242a defined therethrough.

The proximal adjustment assembly 250 includes, a linkage body 252, a flange nut 254 disposed proximally of the linkage body 252, and a coupler 256 disposed distally of the linkage body 252. The linkage body 252 includes a central opening 252a defined therethrough, and a recess 252b defined in a proximal portion of the linkage body 252 between a pair of arms 258 extending along lateral sides of the linkage body 252. The arms 258 include proximal holes 258a that are dimensioned to engage an insertion instrument 20 (see e.g. FIG. 18A) and distal holes 258b that are aligned with the angled slots 220a, 240a of the proximal fins 220, 240 of the upper and lower bodies 210, 230. A first set of pins 251 respectively extends through and frictionally engages the distal hole 258b and the angled slots 220a, 240a of the proximal fins 220, 240 of the upper and lower bodies 210, 230 to adjustably couple the upper and lower bodies 210, 230 together via the linkage body 252. The first set of pins 251 is configured to ride along the angled slots 220a, 240a of the proximal fins 220, 240 of the upper and lower bodies 210, 230 as the linkage body 252 is moved proximally and/or distally within the upper and lower bodies 210, 230.

The coupler 256 includes a central opening 256a defined therein that has the same size and shape as the central opening 252a of the linkage body 252. The central openings 252a and 256a of the linkage body 252 and the coupler 256 are sized and shaped to engage, and be supported on, a shaft 282 of an expander 274 of the distal adjustment assembly 270. The coupler 256 also includes a pair of nubs 260 having flanged outer ends 260a extending laterally from sides thereof that are dimensioned to be retained and slide within the vertical slots 220b, 240b of the proximal fins 220, 240 of the upper and lower bodies 210, 230.

The flange nut 254 includes a body portion 254a having a flanged distal end 254b and a threaded opening 254c defined therethrough that is configured to threadingly engage a threaded post 272 of the distal adjustment assembly 270 and be rotated and axially translated along the threaded post 272. The flanged distal end 254b of the flange nut 254 is dimensioned to be received within the recess 252b of the linkage body 252. Accordingly, movement of the flange nut 254 distally moves the linkage body 252 distally causing the first set of pins 251 to translate within the angled slots 220a, 240a of the proximal fins 220, 240 and the nubs 260 of the coupler 256 to translate within the vertical slots 220b, 240b of the proximal fins 220, 240 to increase the distance between the upper and lower bodies 210 and 230 at the proximal region 200a of the spinal implant 200. Conversely, movement of the flange nut 254 proximally moves the linkage body 252 proximally to reduce the distance between the upper and lower bodies 210, 230 at the proximal region 200a of the spinal implant 200.

The distal adjustment assembly 270 includes a threaded post 272, an expander 274, and a pivot linkage assembly 275 (see e.g., FIG. 15) including an upper pivot linkage 276 and a lower pivot linkage 278. The threaded post 272 includes an elongated threaded body 272a having a hex-shaped proximal end 272b (see e.g., FIG. 12B) configured to mate with a driver 23 of an insertion instrument 20 (see e.g., FIG. 18D) and a distal end 272c. The expander 274 includes a body portion 280 defining a cavity 280a therein. A pair of opposed longitudinal slots 280b is disposed on lateral sides of the body portion 280, and a distal end of the body portion 280 includes a double ramped inner surface 280c (see e.g., FIG. 14C). A shaft 282 extends proximally from the body portion 280 of the expander 274 and defines a threaded opening 282a therethrough that is configured to receive the threaded post 272.

The pivot linkage assembly 275 includes an upper pivot linkage 276 having an upper hole 276a and a lower hole 276b, and a lower pivot linkage 278 having an upper hole 278a and a lower hole 278b. The upper hole 276a of the upper pivot linkage 276 is aligned with the through holes 222a defined in the distal posts 222 of the upper body 210, and a second set of pins 252 is inserted therethrough for pivotably connecting the upper pivot linkage 276 with the upper body 210. The lower hole 278b of the lower pivot linkage 278 is aligned with the through holes 242a defined in the distal posts 242 of the lower body 230, and a pin 255 is inserted therethrough for pivotably connecting the lower pivot linkage 278 with the lower body 230. The lower hole 276b of the upper pivot linkage 276 and the upper hole 278a of the lower pivot linkage 278 are aligned with each other and with the longitudinal slots 280b defined in the expander 274 such that the upper and lower pivot linkages 276 and 278 are disposed within the cavity 280a in the body portion 280 of the expander 274, and a pin 257 is disposed therethrough for pivotably securing the upper and lower bodies 210 and 230 to the expander 274 of the distal adjustment assembly 270 via the upper and lower pivot linkages 276, 278. This arrangement allows for simultaneous translation of the pin 257 within the longitudinal slots 280b of the expander 274 and pivoting movement of the upper and lower pivot linkages 276, 278.

In use, the threaded post 272 is rotated in a first direction to advance the threaded post 272 distally until it pushes against and drives the upper and lower pivot linkages 276, 278 against the double ramped inner surface 280c of the expander 274 thereby increasing the height between the upper and lower bodies 210, 230 at the distal region 200b of the spinal implant 200. Rotation of the threaded post 272 in a second, reverse direction moves the threaded post 272 proximally to allow the upper and lower pivot linkages 276, 278 to collapse, thereby decreasing the height between the upper and lower bodies 210, 230 at the distal region 200b of the spinal implant 200.

Figure 14A:
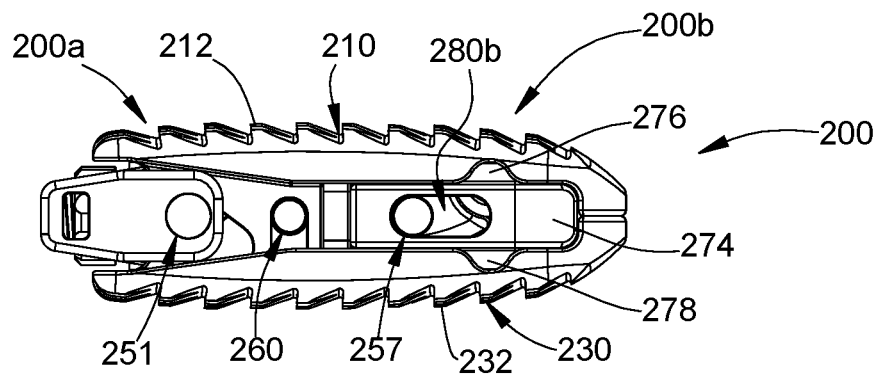
FIGS. 14A-14C are side, top, and cross-sectional views, respectively, of the spinal implant of FIGS. 12A-12B, in a collapsed position.
Figure 14B:
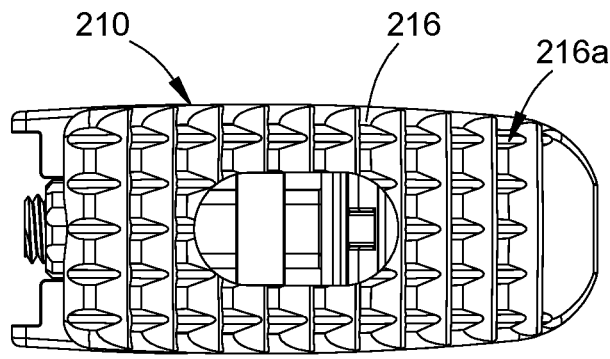
Figure 14C:
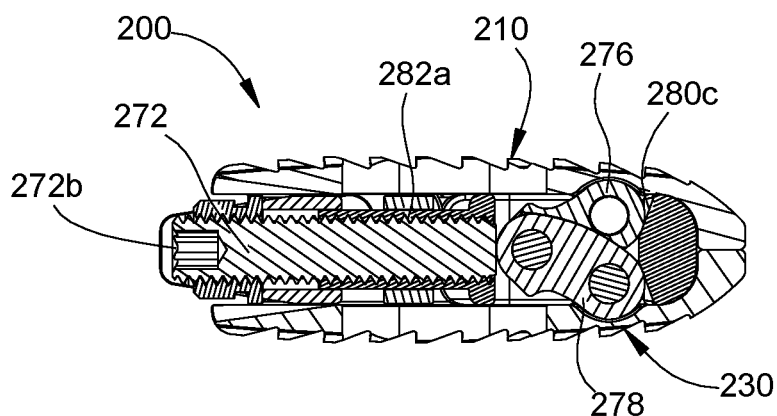

As shown in FIGS. 14A-14C, the spinal implant 200 has a collapsed, or unexpanded, position. In the collapsed position, the planar portions 212, 232 of the upper and lower bodies 210, 230 are disposed in parallel relationship to each other. The first set of pins 251 of the linkage body 252 and the nubs 260 of the coupler 256 are disposed within the angled slots 220a, 240a and the vertical slots 220b, 240b, respectively, of the proximal fins 220, 240 of the upper and lower bodies 210, 230 such that the nubs 260 rest within an uppermost portion of the vertical slot 220a of the upper body 210 and a lowermost portion of the vertical slot 240b of the lower body 230. The pin 257 disposed through the expander 274 and the upper and lower pivot linkages 276, 278 is disposed in a proximalmost position within the longitudinal slots 280b of the expander 274 so that the upper and lower pivot linkages 276, 278 are in the collapsed position.

Figure 15:
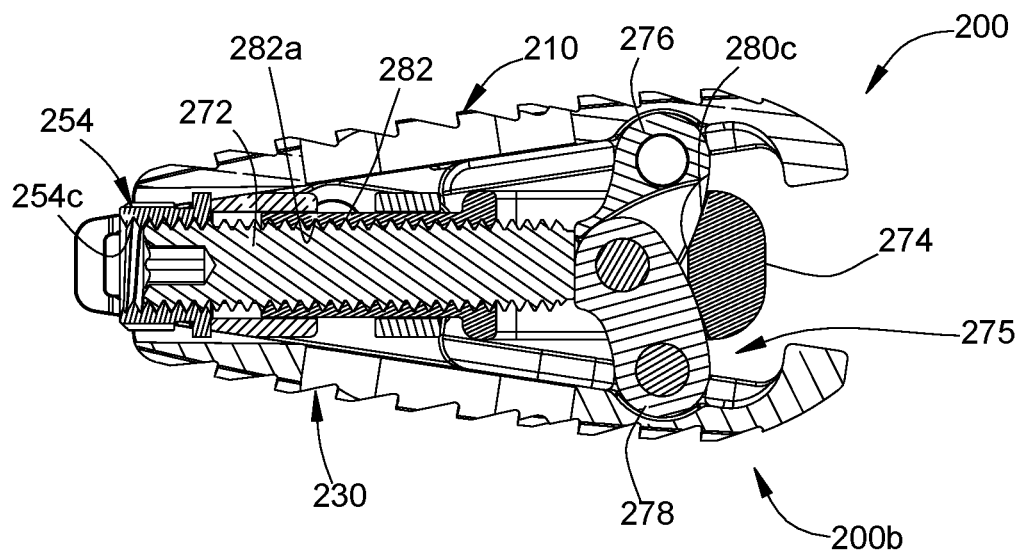
FIG. 15 is a cross-sectional view of the spinal implant of FIGS. 12A-12B, with a distal region of the spinal implant in a partially expanded position.
Figure 16:
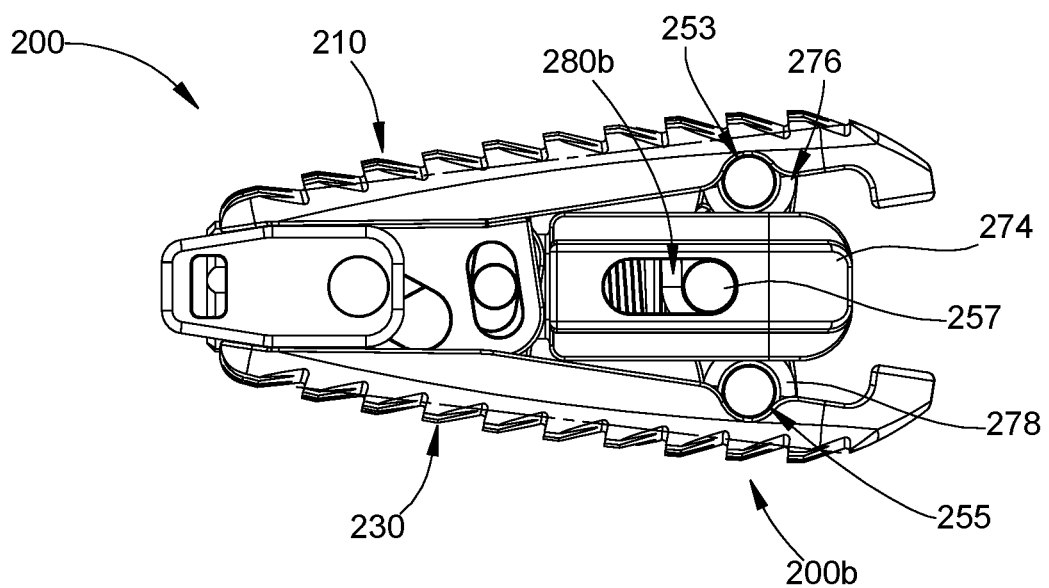
FIG. 16 is a side view of the spinal implant of FIGS. 12A-12B, with a distal region of the spinal implant in a fully expanded position.

As shown in FIG. 15, rotation of the threaded post 272 in a first direction moves the threaded post 272 distally through the threaded opening 254c of the flange nut 254 and the threaded opening 282a of the shaft 282 of the expander 274 which, in turn, pushes the upper and lower pivot linkages 176, 178 into the double ramped inner surface 280c of the expander 274 to change the distance between the upper and lower bodies 210, 230 about the distal region 200b of the spinal implant 200. Continued rotation of the threaded post 272 in the distal direction causes the upper and lower pivot linkages 276, 278 to move into a fully expanded position, as shown in FIG. 16. In the fully expanded state, the pin 257 is disposed in a distalmost position within the longitudinal slot 280b of the expander 274.

Figure 17A:
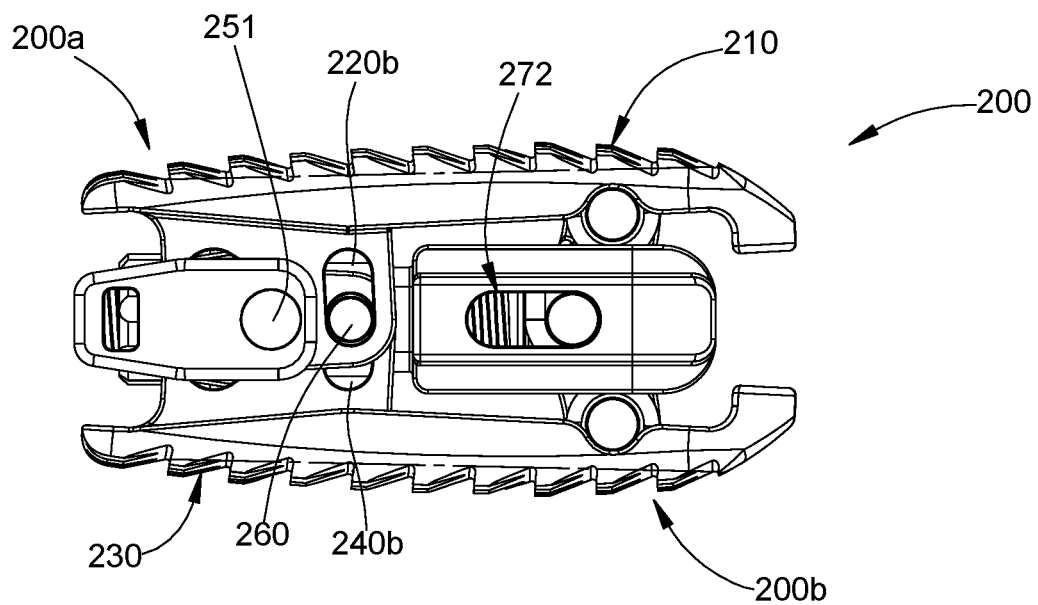
FIGS. 17A and 17B are side and cross-sectional views, respectively, of the spinal implant of FIGS. 12A-12B, with proximal and distal regions of the spinal implant each in a fully expanded position.
Figure 17B:
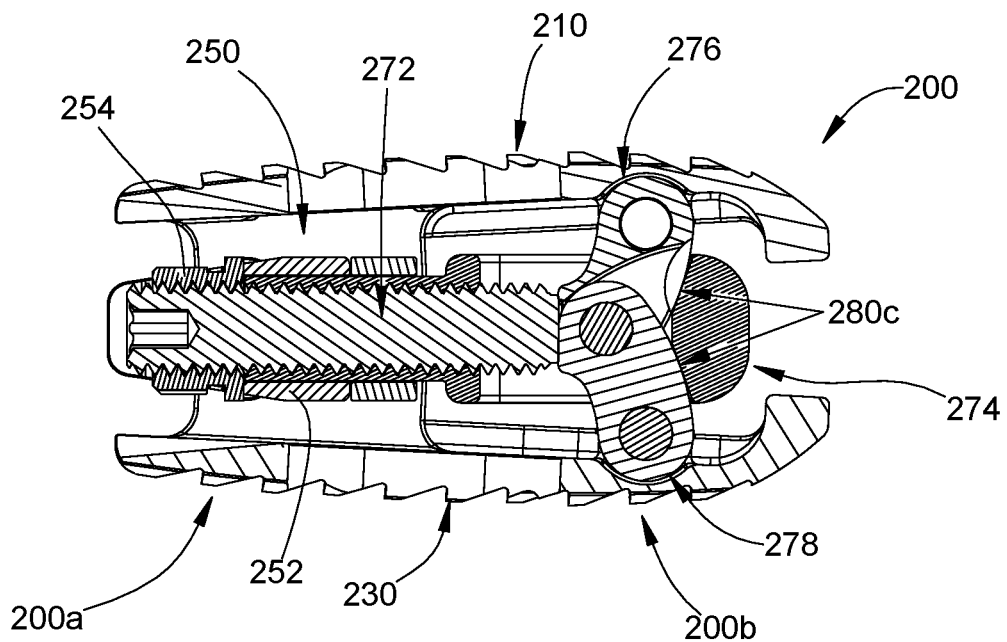

The flange nut 254 of the proximal adjustment assembly 250 may be advanced distally between the upper and lower bodies 210, 230 to drive the upper and lower bodies 210, 230 apart at the proximal region 200a of the spinal implant 200, as shown in FIGS. 17A-17B. Rotation of the flange nut 254 in a first direction moves the flange nut 254 and the linkage body 252 distally such that the first set of pins 251 slide within the angled slots 220a, 240a of the proximal fins 220, 240 of the upper and lower bodies 210 and 230, and the nubs 260 of the coupler 256 slide within the vertical slots 220b, 240b to partially or fully expand the proximal region 200a of the spinal implant 200. The proximal region 200a of the spinal implant 200 is fully expanded when the nubs 260 of the coupler 256 are disposed within a lowermost portion of the vertical slot 220a of the upper body 210 and an uppermost portion of the vertical slot 240b of the lower body 230. While the distal region 200b of the spinal implant 200 is shown in the fully expanded position of FIG. 16, it should be understood that the distal region 200b may have any desired configuration.

Figure 18A:
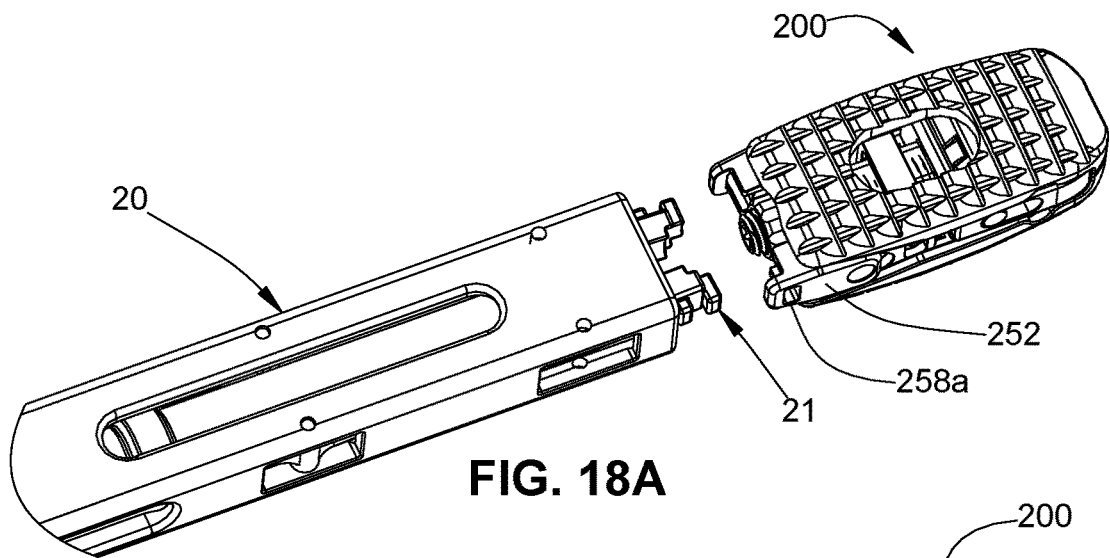
Figure 18B:
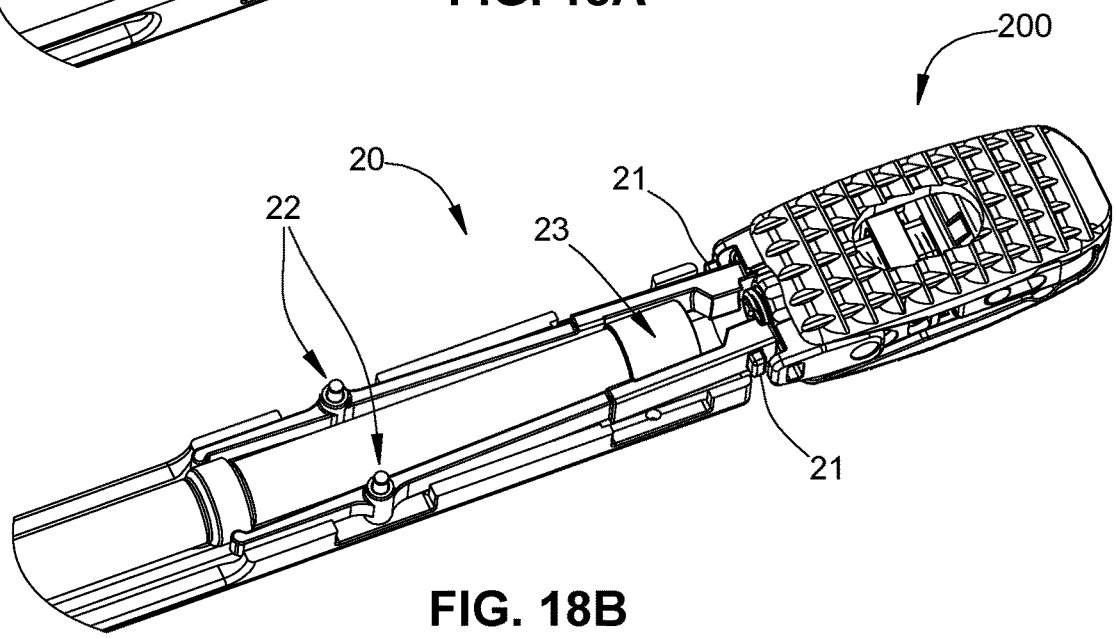
Figure 18C:
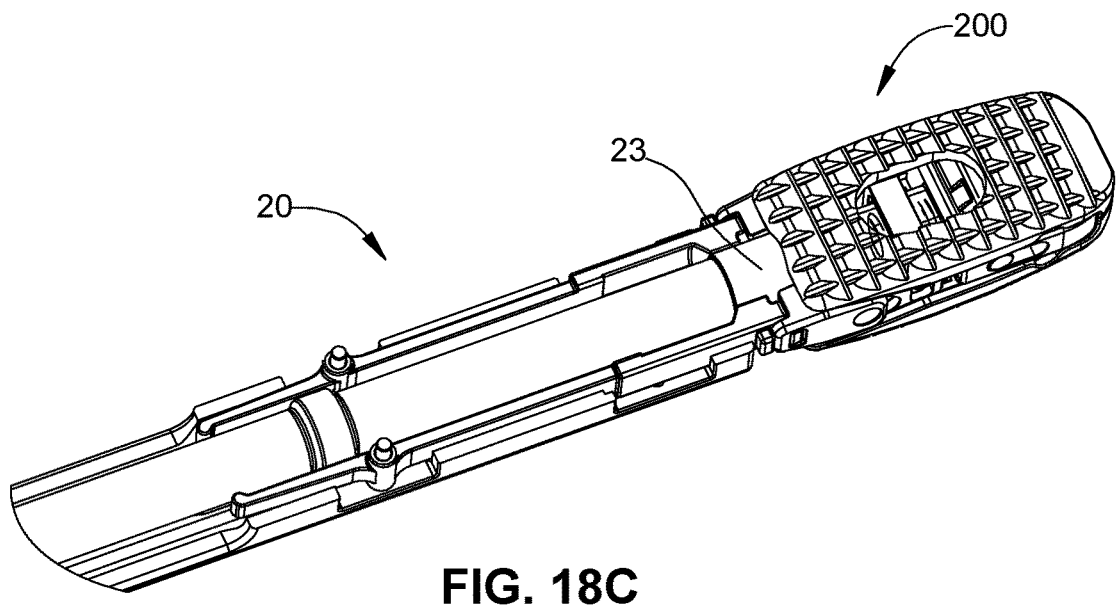

Referring now to FIGS. 18A-18E, the spinal implant 200 and an insertion instrument 20 are shown. As shown in FIG. 18A, the insertion instrument 20 includes feet 21 disposed at a distal end thereof that are configured to engage the proximal through holes 258a of the linkage body 252 of the spinal implant 200. As shown in FIG. 18B, the insertion instrument 20 includes hinges 22 that allow the feet 21 to flex for releasable positioning of the feet 21 into the proximal through holes 258a of the spinal implant 200. As shown in FIGS. 18C-18E, a driver 23 is inserted through an opening 20a of the insertion instrument 20, and includes a shaped distal end 24, such as a hex portion, configured to make with the hex-shaped proximal end 272b of the threaded post 272. A handle 25 of the driver 23 is rotated in a first or second direction to rotate the threaded post 272 which, in turn, moves the threaded post 272 distally or proximally to adjust the height of the distal region 200b of the spinal implant 200.

A thumb wheel 26 of the insertion instrument 20 is rotated in a first or second direction to rotate the flange nut 254 which, in turn, moves the flange nut 254 distally or proximally to adjust the height of the proximal region 200a of the spinal implant 200.

In use, a clinician removes all or a portion of a disc from between two vertebral bodies (e.g., complete or partial diskectomy) and cleans the end plates of the vertebral bodies, as discussed above. The clinician then places the spinal implant 200 into the disc space using the insertion instrument 20, and may adjust the height of the proximal and/or distal regions 200a and 200b of the spinal implant 200 as described above. Various allograft and/or autograft materials may be used to assist in the fusion process.

Figure 19:
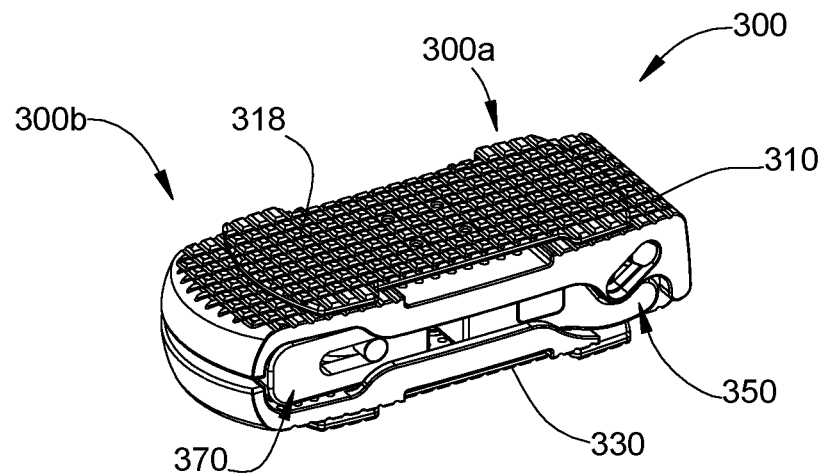
FIG. 19 is a perspective view of a spinal implant in accordance with another embodiment of the present disclosure, with wing portions of the spinal implant in a retracted position.
Figure 20:
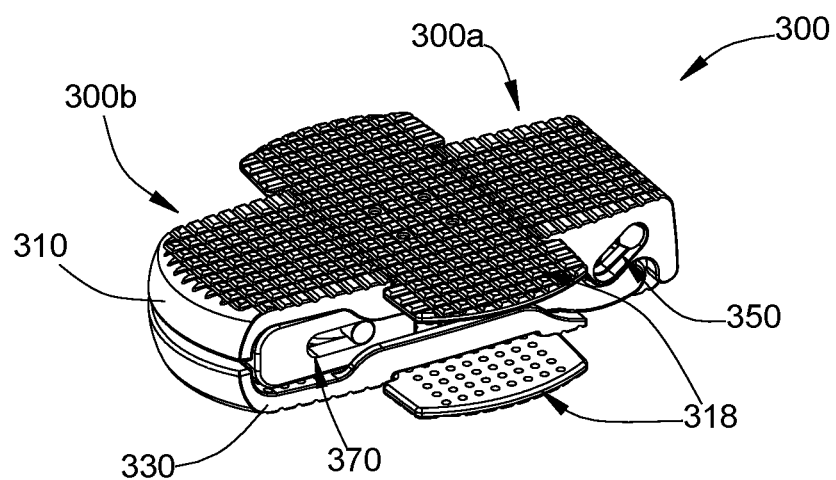
FIG. 20 is a perspective view of the spinal implant of FIG. 19, with the wing portions of the spinal implant in a deployed position.

Referring now to FIGS. 19 and 20, an expandable spinal implant or spinal implant 300 in accordance with another embodiment of the present disclosure is shown. The spinal implant 300 is similar to spinal implants 100 and 200, and thus will be described with respect to the differences therebetween.

The spinal implant 300 has a proximal region 300a and a distal region 300b, and includes an upper body 310 and a lower body 330 disposed in opposed relation relative to each other and coupled together by a proximal adjustment assembly 350 and a distal adjustment assembly 370. The proximal and distal adjustment assemblies 350 and 370 are independently movable to allow for adjustment in the angular and vertical distance between the upper and lower bodies 310 and 330 of the proximal and distal regions 300a and 300b of the spinal implant 300.

The independent adjustability of the proximal and distal regions 300a, 300b of the spinal implant 300 allows a clinician to adjust the dimensions of the spinal implant 300 (i.e., vertical heights of the proximal and distal regions) such that the spinal implant 300 can be inserted between two vertebrae with relatively narrow access in the collapsed position, without force, to avoid trauma to the vertebral bodies, and in particular, the endplates of the vertebral bodies. The proximal and/or distal regions 300a, 300b of the spinal implant 300 can then be adjusted to partially or fully expanded positions so that the upper and lower bodies 310, 330 are aligned with the endplates to maximize surface contact between the spinal implant 300 and the endplates, and to match the dimensions of the disc space defined between the endplates of the vertebral bodies in which the spinal implant 300 is disposed. The adjustability of the spinal implant 300 allows a clinician, for example, to minimize trauma to the vertebrae during implantation of the spinal implant 300, to tailor the spinal implant 300 to conform to the anatomy of individual patients, to maximize contact between the spinal implant 300 and the endplates to create bone growth, to match the natural disc height of the disc space, to improve the seating of the spinal implant 300 within the disc space, and/or to lessen the likelihood of expulsion of the spinal implant 300 from the disc space.

Figure 21:
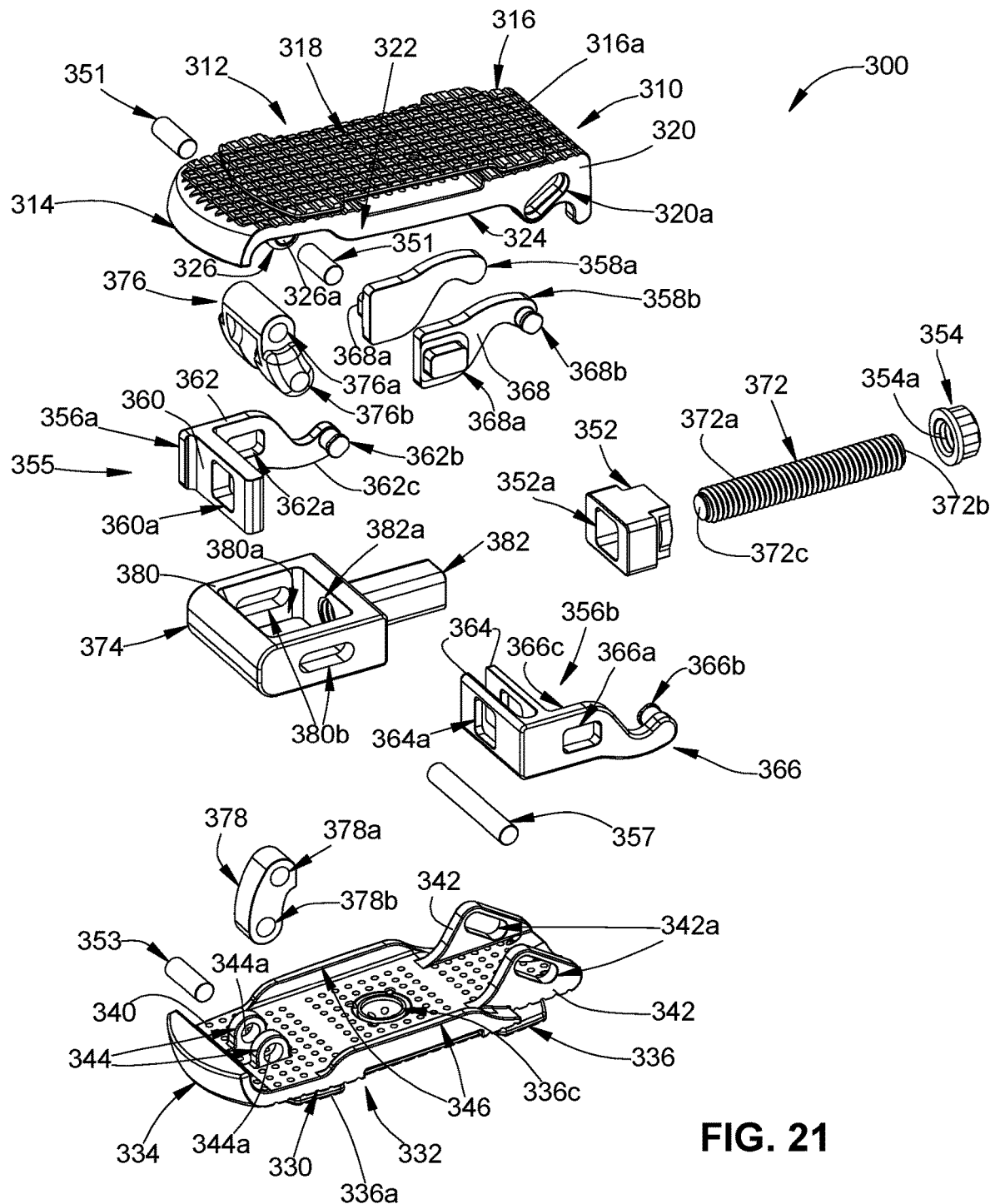
FIG. 21 is an exploded view of the spinal implant of FIG. 19.
Figure 22A:
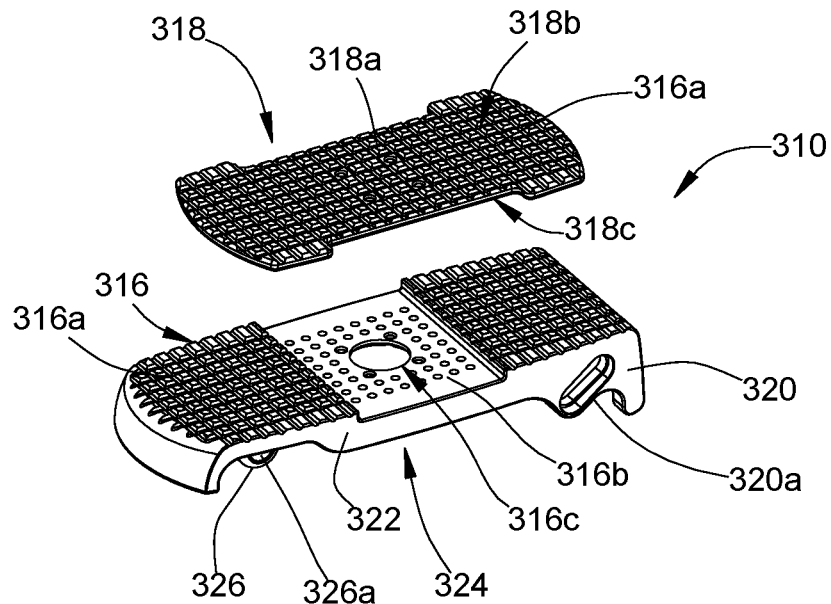
FIGS. 22A and 22B are perspective views of an upper body and a lower body, respectively, of the spinal implant of FIG. 19, with parts separated.
Figure 22B:
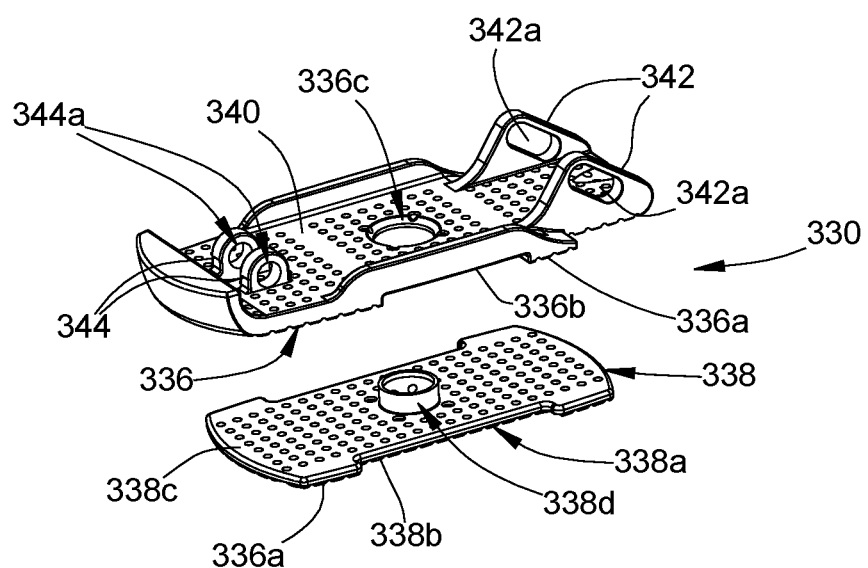

Turning now to FIGS. 21, 22a, and 22b, the upper body 310 of the spinal implant 300 includes an elongated substantially planar portion 312 and a curved portion 314 disposed distally of the planar portion 312. The planar portion 312 is a two-piece construction including an outer surface 316 and a wing portion 318 disposed over the outer surface 316. The outer surface 316 includes a plurality of retaining features 316a and a central recess 316b including an opening 316c defined therein. The wing portion 318 includes an elongated body 318a including an outer surface 318b including a plurality of retaining features 316a, and an inner surface 318c including a flange (not shown) extending therefrom that is dimensioned to be received and retained within the opening 316c of the outer surface 316 (e.g., the flange may be swaged or rolled into securement with upper body 310 to prevent separation of the wing portion 318 from the outer surface 316 of the upper body 310).

The wing portion 318 is movable from a first, retracted position in which the wing portion 318 is aligned with the outer surface 316 of the upper body 310 (see e.g., FIG. 19) and a second, deployed position in which the wing portion 318 is turned or rotated 90 degrees and disposed within the central recess 316b defined in the outer surface 316 of the upper body 310 (see e.g., FIG. 20) such that the wing portion 318 is flush with the outer surface 316 to increase the surface area and footprint of the outer surface 316 of the upper body 310. It should be understood that the planar portion 312 of the upper body 310 may be a one piece construction, as shown, for example in the embodiments of spinal implants 100 and 200. Angled slots 320a are disposed in a proximal portion of side surfaces 320 of the upper body 310, and rib features 322 extends from the side surface 320 to strengthen the upper body 310. An inner surface 324 of the upper body 310 includes a pair of distal posts 326 each including a through hole 326a defined therethrough.

The lower body 330 of the spinal implant 300 includes an elongated substantially planar portion 332 and a curved portion 334 disposed distal to the planar portion 332. The planar portion 332 is a two-piece construction including an outer surface 336 and a wing portion 338 disposed over the outer surface 336. The outer surface 336 includes a plurality of retaining features 336a and a central recess 336b including an opening 336c defined therein. The wing portion 338 includes an elongated body 338a including an outer surface 338b including a plurality of retaining features 336a, and an inner surface 338c including a flange 338d extending therefrom that is dimensioned to be received within the opening 336c of the outer surface 336, as described above with respect to the wing portion 318 of the upper body 310.

The wing portion 338 is movable from a first, retracted position in which the wing portion 338 is aligned with the outer surface 336 of the lower body 330 (see e.g., FIG. 19) and a second, deployed position in which the wing portion 338 is turned 90 degrees and disposed within the central recess 336b defined in the outer surface 336 of the lower body 330 (see e.g., FIG. 20) such that the wing portion 338 is flush with the outer surface 336 to increase the surface area and footprint of outer surface 336 of the lower body 330. It should be understood that the planar portion 332 of the lower body 330 may be a one piece construction, as shown, for example in the embodiments of spinal implants 100 and 200. An inner surface 340 of the lower body 330 includes a pair of proximal fins 342 including angled slots 342a defined therethrough, and a pair of distal posts 344 each including a through hole 344a defined therethrough. Rib features 346 extend from lateral sides of the lower body 330 to strengthen the lower body 330.

Referring again to FIG. 21, the proximal adjustment assembly 350 includes a plug 352, a nut 354 disposed distal to the plug 352, and a bracket assembly 355 including first and second bracket bodies 356a, 356b, and first and second bracket arms 358a, 358b. The plug 352 includes a central opening 352a defined therethrough that is configured to engaged and slide relative to a shaft 382 of an expander 374 of the distal adjustment assembly 370. The first bracket body 356a has an L-shape and includes a plate 360 having an opening 360a defined therethrough, and an extension 362 extending proximally therefrom that includes an opening 362a defined therethrough and a proximal nub 362b extending from an inner surface 362c of the extension 362. The second bracket body 356b also has an L-shape and includes a pair of spaced plates 364 having openings 364a defined therethrough, and an extension 366 extending proximally therefrom that includes an opening 366a defined therethrough and a proximal nub 366b extending from an inner surface 366c of the extension 366. The plate 360 of the first bracket body 356a is received between the plates 364 of the second bracket body 356b such that the openings 360a and 364a are aligned and slidably engaged with the shaft 382 of the expander 374 of the distal adjustment assembly 370.

The first and second bracket arm 358a, 358b include outer surfaces 368 each including a distal boss 368a and a proximal nub 368b. The distal bosses 368a of the first and second bracket arms 358a, 358b are dimensioned to be received and retaining within the openings 362a, 366a of respective extensions 362, 366 of the first and second bracket bodies 356a, 356b. The proximal nubs 368a of the first and second bracket arms 358a and 358b are dimensioned to be received and slidably retained within the angled slots 320a of the upper body 310, and the proximal nubs 362b, 366b of the extensions 362, 366 of the first and second bracket bodies 356a, 356b are dimensioned to be received and slidably retained within the angled slots 342a defined in the proximal fins 342 of the lower body 330. Thus, the upper and lower bodies 310, 330 are coupled together via the bracket assembly 355 of the proximal adjustment assembly 350.

The nut 354 includes a threaded opening 354a that is configured to threadingly engage a threaded post 372 of the distal adjustment assembly 370, and be rotated and axially translated along the threaded post 372. Accordingly, distal movement of the nut 354 pushes and slides the plug 352 and the bracket assembly 355 distally along the shaft 382 of the expander 374 which, in turn, slides the proximal nubs 368b disposed within the angled slots 320a of the upper body 310, and the proximal nubs 362b, 366b disposed within the angled slots 342a of the lower body 330, to increase the distance between the upper and lower bodies 310 and 330 at the proximal region 300a of the spinal implant 300.

The distal adjustment assembly 370 includes a threaded post 372, an expander 374, and a pivot linkage assembly 375 (see e.g., FIG. 25C) including an upper pivot linkage 376 and a lower pivot linkage 378. The threaded post 372 includes an elongated threaded body 372a having a shaped proximal end 372b (see e.g., FIG. 26C) configured to mate with an insertion instrument (not shown) and a distal end 372c. The expander 374 includes a body portion 380 defining a cavity 380a therein. A pair of opposed longitudinal slots 380b are disposed on lateral sides of the body portion 380, and a distal end of the body portion 380 includes a double ramped inner surface 380c (see e.g., FIG. 26C). A shaft 382 extends proximally from the body portion 380 and defines a threaded opening 382a therethrough that is configured to receive the threaded post 372.

The pivot linkage assembly 375 includes an upper pivot linkage 376 having an upper hole 376a and a lower hole 376b, and a lower pivot linkage 378 having an upper hole 378a and a lower hole 378b. The upper hole 376a of the upper pivot linkage 376 is aligned with the through holes 326a defined in the distal posts 326 of the upper body 310, and a first set of pins 351 are inserted therethrough for pivotably connecting the upper pivot linkage 376 with the upper body 310. The lower hole 378b of the lower pivot linkage 378 is aligned with the through holes 344a defined in the distal posts 344 of the lower body 330, and a pin 353 is inserted therethrough for pivotably connecting the lower pivot linkage 378 with the lower body 330. The lower hole 376b of the upper pivot linkage 376 and the upper hole 378a of the lower pivot linkage 378 are aligned with the longitudinal slots 380b defined in the expander 374 such that the upper and lower pivot linkages 376 and 378 are disposed within the cavity 380a in the body portion 380 of the expander 374, and a pin 357 is disposed therethrough for pivotably securing the upper and lower bodies 310 and 330 to the expander 374 of the distal adjustment assembly 370 via the upper and lower pivot linkages 376 and 378.

In use, the threaded post 372 is advanced distally through the threaded opening 382a of the shaft 382 of the expander 374, and into the cavity 380a defined in the body portion 380 of the expander 374 until it contacts and pushes the upper and lower pivot linkages 376, 378 against the double ramped inner surface 380c of the expander 374 thereby increasing the height between the upper and lower bodies 310, 330 at the distal region 300b of the spinal implant 300. Movement of the threaded post 372 in a reverse direction allows the upper and lower pivot linkages 376, 378 to collapse, thereby decreasing the height between the upper and lower bodies 310, 330 at the distal region 300b of the spinal implant 300.

As shown in FIGS. 23A-24B, the spinal implant 300 has a collapsed, or unexpanded, position. In the collapsed position, the planar portions 312, 332 of the upper and lower bodies 310, 330 are disposed in parallel relationship to each other. Each of the proximal and distal regions 300a, 300b of the spinal implant 300 has a height, "h5," that defines the minimum distance at which the upper and lower bodies 310, 330 may be positioned relative to each other, and each of the wing portions 318, 338 has a height, "h6," that defines the minimum distance at which the wing portions 318, 338 may be positioned relative to each other when in the retracted position. In embodiments, the height, "h5," may range from about 2.5 mm to about 12.5 mm, and the height, "h6," may range from about 4 mm to about 14 mm. The proximal nubs 368b of the bracket arms 358a, 358b are disposed within an uppermost portion of the angled slots 320a of the upper body 310 and the proximal nubs 362b, 366b of the bracket bodies 356a, 356b are disposed within a lowermost portion of the angled slots 342a of the lower body 330. The pin 357 disposed through the expander 374 and the upper and lower pivot linkages 376 and 378 is disposed in a proximalmost position within the longitudinal slots 380b of the expander 374 so that the upper and lower pivot linkages 376 and 378 are in the collapsed position.

Figure 23A:
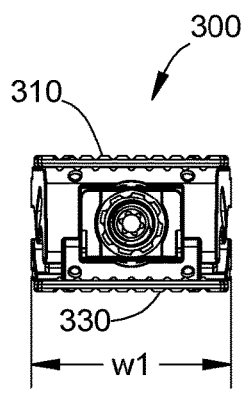
FIGS. 23A and 23B are end and side views, respectively, of the spinal implant of FIG. 19, in a collapsed position.
Figure 23B:
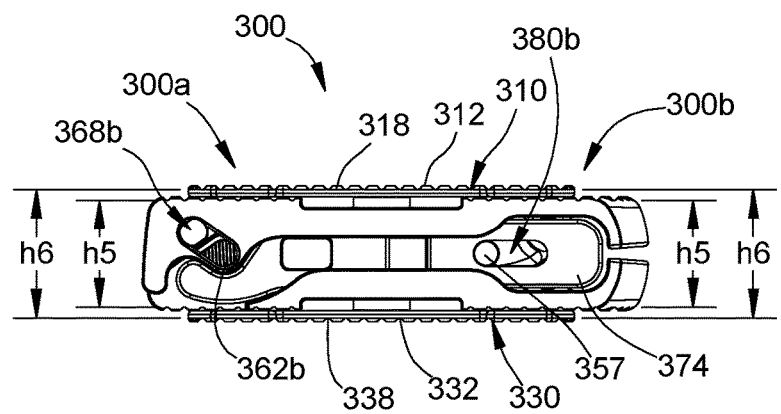
Figure 24A:
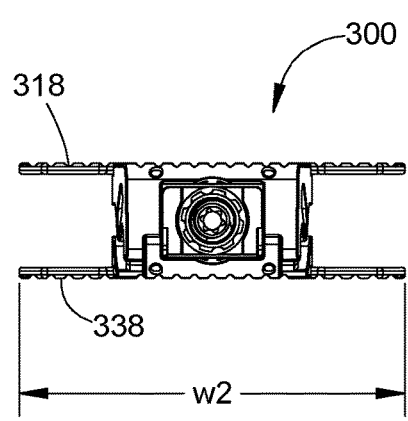
FIGS. 24A and 24B are end and side views, respectively, of the spinal implant of FIGS. 23A and 23B, with the wing portions in a deployed position.
Figure 24B:
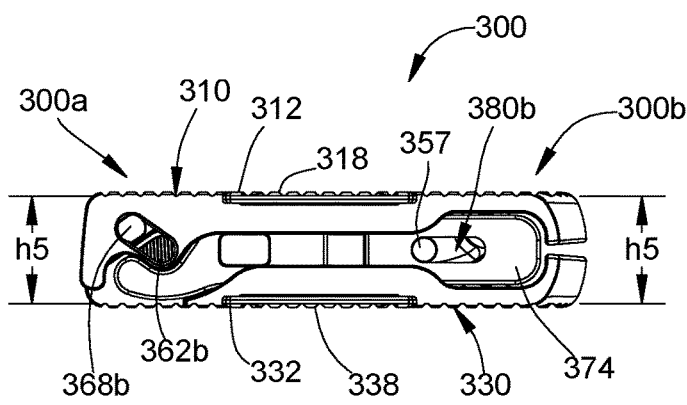

In the embodiment of FIGS. 23A and 23B, the wing portions 318, 338 of the upper and lower bodies 310, 330 are in the retracted position such that the spinal implant 300 has an unexpanded width, "w1," and in the embodiment of FIGS. 24A and 24B, the wing portions 318, 338 of the upper and lower bodies 310, 330 are in the deployed position, such that the spinal implant 300 has an expanded width, "w2." In embodiments, the width, "w1," may range from about 9 mm to about 19 mm, and the width, "w2," may range from about 22 mm to about 32 mm. Accordingly, in the retracted position, the spinal implant 300 has an increased overall height and a decreased width compared to the deployed position.

The wing portions 318, 338 may be deployed independently or at the same time and/or may be deployed at varying angles with respect to the upper and lower bodies 310 and 330. The wing portions 318, 338 are deployed manually after insertion of the spinal implant 300 into a disc space, however, it is contemplated that the wing portions 318, 338 may be deployed manually prior to insertion of the spinal implant 300 into the disc space. The wing portions 318, 338 may be deployed with the use of a tether or the like and then reversed back into alignment with the upper and lower bodies 310, 330.

As shown in FIG. 25A-25C, with the proximal region 300a of the spinal implant 300 in a collapsed position having a height, "h7," rotation of the threaded post 372 in a first direction moves the threaded post 372 distally and into contact with the upper and lower pivot linkages 376 and 378 which, in turn, pushes the upper and lower pivot linkages 376 and 378 into the double ramped inner surface 380c (see e.g., FIG. 26C) of the expander 374 to change the distance between the upper and lower bodies 310 and 330 about the distal region 300b of the spinal implant 300. Continued rotation of the threaded post 372 in the distal direction causes the upper and lower pivot linkages 376 and 378 to move into a fully expanded position in which the distal region 300b has a height, "h8," that forms an acute angle, "θ1," with respect to a plane extending along the upper or lower body 310, 330. In embodiments, the height, "h7," may range from about 2 mm to about 12 mm, the height, "h8," may range from about 9 mm to about 19 mm, and the angle, "θ1," may range from about 8° to about 18°. In the fully expanded position, the pin 357 is disposed in a distalmost position within the longitudinal slot 380b of the expander 374.

Figure 26A:
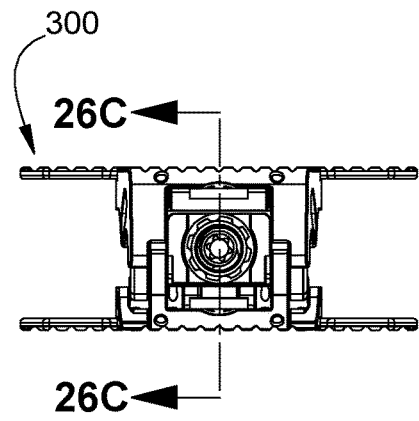
FIGS. 26A-26C are end, side, and cross-sectional views, respectively, of the spinal implant of FIG. 19, with a proximal region of the spinal implant in a fully expanded position and a distal region of the spinal implant in a partially expanded position.
Figure 26B:
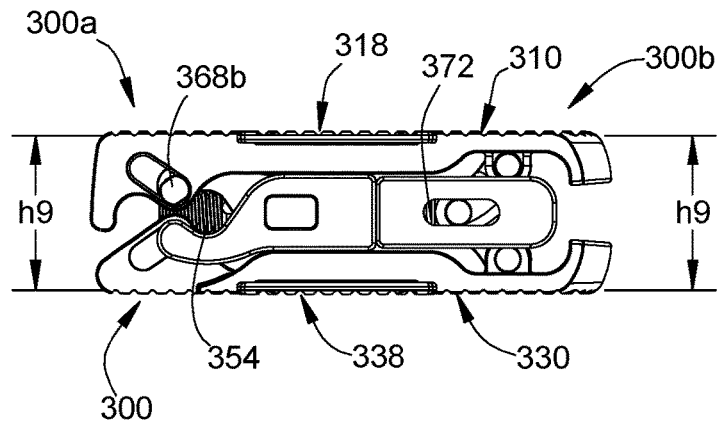
Figure 26C:
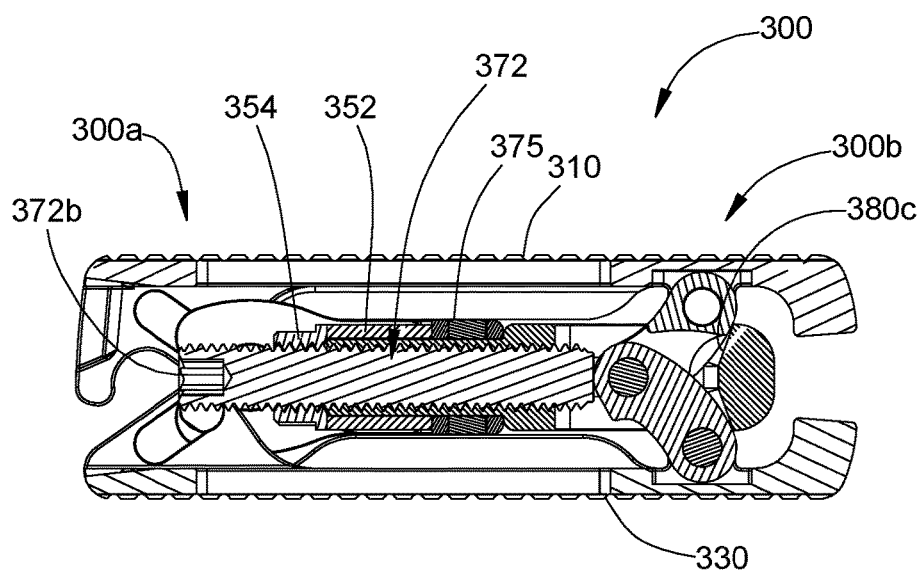

As shown in FIGS. 26A-26C, the distal region 300b of the spinal implant 300 is shown in a partially expanded position due to rotation of the threaded post 372, as described above. The proximal region 300a of the spinal implant 300 is also partially expanded by rotating the nut 354 distally along the threaded post 372 such that the nut 354 abuts the plug 352 and pushes the plug 352 into the bracket assembly 355 thereby sliding the nubs 368b in the angled slots 320a of the upper body 310 and the nubs 362b and 366b in the angled slots 342a of the lower body 330, causing the upper and lower bodies 310 and 330 to move apart about the proximal region 330a of the spinal implant 300. The proximal and distal regions 300a and 300b are shown as having the same height, "h9." In embodiments, the height, "h9," may range from about 5.5 mm to about 15.5 mm. It should be understood that the proximal and distal regions 300a and 300b may be adjusted alone or in combinations of the same or different heights. As shown in FIGS. 27A-27C, the proximal region 300a of the spinal implant 300 is fully expanded to a height, "h10," and the distal region 300b of the spinal implant 300 is fully expanded to a height, "h11," such that the spinal implant 300 has a lordotic shape. In embodiments, the height, "h10," may range from about 5 mm to about 15 mm, and the height "h11," may range from about 9 mm to about 19 mm. The angle, "θ2," defined at the distal region 300b of the spinal implant 300 may range from about 1° to about 11°.

In use, a clinician remove all or a portion of the disc from between the two vertebral bodies (e.g., complete or partial diskectomy) and cleans the endplates of the vertebral bodies, as discussed above. Next, the clinician places the implant 300 into the disc space using an insertion instrument (not shown). Next, the wing portions may be deployed depending on surgical need. Various allograft and/or autograft materials may be used to assist in the fusion process. Should the clinician need to adjust the height of the implant 300 after it is inserted between the vertebrae, the proximal and/or distal heights can be adjusted independently, as discussed above with respect to spinal implants 100, 200.

While embodiments shown and described herein illustrate exemplary heights and/or widths of the spinal implant in collapsed, partially expanded, and fully expanded positions, it should be understood that other unexpanded and expanded heights and/or widths are also contemplated.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

The invention claimed is:

1. A spinal implant extending along a longitudinal axis between a proximal region and a distal region, the spinal implant comprising:
    an upper body for engaging an upper vertebral body;
    a lower body for engaging a lower vertebral body;
    a proximal adjustment assembly disposed between the upper and lower bodies in the proximal region of the spinal implant and adjustably coupled to the upper and lower bodies, the proximal adjustment assembly including a proximal member and a proximal rotational actuator, wherein the proximal rotational actuator includes a threaded portion, such that the proximal adjustment assembly is actuated by driving threaded advancement of the proximal rotational actuator, whereby the proximal member is induced to translate along the longitudinal axis; and
    a distal adjustment assembly disposed between the upper and lower bodies in the distal region of the spinal implant and adjustably coupled to the upper and lower bodies, the distal adjustment assembly including a distal member and a distal rotational actuator, wherein the distal rotational actuator includes a threaded portion, such that the distal adjustment assembly is actuated by driving threaded advancement of the distal rotational actuator, whereby the distal member is induced to translate along the longitudinal axis while the distal member engages and travels along a distal slot of the spinal implant;
    wherein the proximal rotational actuator and the distal rotational actuator are coaxially arranged with respect to one another, actuation of the proximal adjustment assembly drives a change in vertical height between the upper body and the lower body in at least the proximal region, and actuation of the distal adjustment assembly drives a change in vertical height between the upper body and the lower body in at least the distal region, and
    wherein the proximal rotational actuator and the distal rotational actuator each include a respective actuation interface for engagement by one or more tools to drive the threaded advancement of the respective proximal and distal rotational actuator, and wherein the actuation interfaces of the proximal and distal rotational actuators are positioned in the proximal region of the spinal implant.

2. The spinal implant of claim 1, wherein the threaded advancement of the proximal rotational actuator and the threaded advancement of the distal rotational actuator are along the longitudinal axis.

3. The spinal implant of claim 1, wherein the proximal rotational actuator and the distal rotational actuator are coaxially arranged with respect to one another such that the proximal rotational actuator is positioned around the distal rotational actuator and such that the proximal rotational actuator and the distal rotational actuator are oriented along the longitudinal axis.

4. The spinal implant of claim 1, wherein the proximal adjustment assembly has a passageway extending therethrough along the longitudinal axis, and wherein a portion of the distal adjustment assembly extends through the passageway.

5. The spinal implant of claim 4, wherein the proximal member has a central opening defined therethrough, the central opening defining at least a portion of the passageway.

6. The spinal implant of claim 4, wherein the proximal rotational actuator has an opening defined therethrough, the opening defining at least a portion of the passageway.

7. The spinal implant of claim 6, wherein the opening includes internal threads, such that the threaded advancement of the proximal rotational actuator is along the internal threads.

8. The spinal implant of claim 7, wherein the internal threads are configured to threadedly engage the portion of the distal adjustment assembly extending through the passageway.

9. The spinal implant of claim 8, wherein the distal rotational actuator includes the portion of the distal adjustment assembly threadedly engaged by the internal threads of the proximal rotational actuator.

10. The spinal implant of claim 1, wherein the distal adjustment assembly and the proximal adjustment assembly are actuatable independently from one another.

11. The spinal implant of claim 1, wherein the proximal member engages and travels along a proximal slot of the spinal implant during actuation of the proximal adjustment assembly so as to drive the change in vertical height between the upper body and the lower body in at least the proximal region of the spinal implant.

12. The spinal implant of claim 1, wherein the proximal member engages and travels along a proximal slot of the spinal implant during actuation of the proximal adjustment assembly, and wherein at least one of the upper body and the lower body includes a first fin extending towards the other of the upper body and the lower body, the proximal slot being defined in the first fin.

13. The spinal implant of claim 12, wherein the proximal slot extends at an oblique angle to the longitudinal axis.

14. The spinal implant of claim 12, wherein the first fin defines at least one vertical slot extending orthogonally to the longitudinal axis.

15. The spinal implant of claim 12, wherein the other of the upper body and the lower body includes a second fin extending towards the first fin.

16. The spinal implant of claim 15, wherein a second proximal slot is defined in the second fin, wherein each of the proximal slot and the second proximal slot extends at a respective oblique angle to the longitudinal axis, and wherein the proximal member includes a pin configured to be received within and to travel along both the proximal slot and the second proximal slot.

17. The spinal implant of claim 15, wherein the at least one of the upper body and the lower body includes the first fin and a third fin extending towards the other of the upper body and the lower body, wherein the other of the upper body and the lower body includes the second fin extending towards the first fin and a fourth fin extending towards the third fin, wherein the first fin and the second fin are positioned on a first side of the longitudinal axis, and the third fin and the fourth fin are positioned on a second side of the longitudinal axis, the second side being opposed to the first side across the longitudinal axis such that an interior space is defined in a region between the first and second fins on the first side and the third and fourth fins on the second side, and wherein the proximal adjustment assembly and the distal adjustment assembly are disposed in the interior space.

18. The spinal implant of claim 1, wherein the distal slot is oriented substantially parallel to the longitudinal axis.

19. The spinal implant of claim 1, wherein the distal adjustment assembly includes first and second pivot linkages.

* * * * *